(12) United States Patent
Bell et al.

(10) Patent No.: US 9,656,261 B2
(45) Date of Patent: May 23, 2017

(54) DNA ANALYZER

(75) Inventors: H. Randall Bell, Arlington, VA (US); Joan M Bienvenue, Fredericksburg, VA (US); John W Pettit, Derwood, MD (US); James P Landers, Charlottesville, VA (US); Jessica V Norris, Palmyra, VA (US); Orion N Scott, Charlottesville, VA (US); Daniel J Marchiarullo, North Haledon, NJ (US); Daniel C Leslie, Brookline, MA (US)

(73) Assignees: LEIDOS INNOVATIONS TECHNOLOGY, INC., Gaithersburg, MD (US); ZyGEM CORPORATION LTD., Hamilton (NZ); UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 0 days.

(21) Appl. No.: 13/064,094

(22) Filed: Mar. 4, 2011

(65) Prior Publication Data

US 2011/0229898 A1    Sep. 22, 2011

Related U.S. Application Data

(63) Continuation of application No. 12/659,488, filed on Mar. 10, 2010, now abandoned.
(Continued)

(51) Int. Cl.
*C12Q 1/68* (2006.01)
*B01L 3/00* (2006.01)
(Continued)

(52) U.S. Cl.
CPC ......... *B01L 3/502753* (2013.01); *B01L 7/525* (2013.01); *G01N 27/44791* (2013.01);
(Continued)

(58) Field of Classification Search
None
See application file for complete search history.

(56) References Cited

U.S. PATENT DOCUMENTS 2,654,387 A    10/1953  Innes
3,357,233 A    12/1967  Roof
(Continued)

FOREIGN PATENT DOCUMENTS

DE    195 49 052 A1    7/1996
EP    0 356 160 A2    2/1990
(Continued)

OTHER PUBLICATIONS

Easley et al. (Lab Chip, 2006, vol. 6, p. 601-610).*
(Continued)

*Primary Examiner* — Stephanie K Mummert
(74) *Attorney, Agent, or Firm* — Oblon, McClelland, Maier & Neustadt, L.L.P.

(57) ABSTRACT

Aspects of the disclosure provide a microfluidic chip to facilitate DNA analysis. The microfluidic chip includes a first domain configured for polymerase chain reaction (PCR) amplification of DNA fragments, a dilution domain coupled to the first domain to dilute a PCR mixture received from the first domain, and a second domain that is coupled to the dilution domain so as to receive the amplified DNA fragments. The second domain includes a separation channel that is configured to perform electrophoretic separation of the amplified DNA fragments. In addition, the disclosure provides a DNA analyzer to act on the microfluidic chip to perform an integrated single chip DNA analysis.

19 Claims, 8 Drawing Sheets

Related U.S. Application Data

(60) Provisional application No. 61/213,404, filed on Jun. 4, 2009, provisional application No. 61/213,405, filed on Jun. 4, 2009, provisional application No. 61/213,406, filed on Jun. 4, 2009.

(51) Int. Cl.
*B01L 7/00* (2006.01)
*G01N 27/447* (2006.01)
*G01N 29/32* (2006.01)
*G01N 21/41* (2006.01)

(52) U.S. Cl.
CPC . *B01L 2300/087* (2013.01); *B01L 2300/0816* (2013.01); *B01L 2400/0421* (2013.01); *G01N 29/32* (2013.01); *G01N 2021/4186* (2013.01)

(56) References Cited

U.S. PATENT DOCUMENTS

| | | |
|---|---|---|
| 3,404,869 A | 10/1968 | Harder |
| 3,459,407 A | 8/1969 | Halzehurst et al. |
| 3,799,742 A | 3/1974 | Coleman |
| 3,857,551 A | 12/1974 | Troy |
| 3,918,908 A | 11/1975 | Moyer et al. |
| 3,924,989 A | 12/1975 | Althausen et al. |
| 3,927,868 A | 12/1975 | Moore |
| 4,088,448 A | 5/1978 | Lilja et al. |
| 4,390,403 A | 6/1983 | Batchelder |
| 4,443,408 A | 4/1984 | Mintz |
| 4,534,659 A | 8/1985 | Dourdeville et al. |
| 4,554,839 A | 11/1985 | Hwewtt et al. |
| 4,675,300 A | 6/1987 | Zare et al. |
| 4,680,201 A | 7/1987 | Hjerten |
| 4,737,464 A | 4/1988 | McConnell et al. |
| 4,740,708 A | 4/1988 | Batchelder |
| 4,756,884 A | 7/1988 | Hillman |
| 4,790,640 A | 12/1988 | Nason |
| 4,849,340 A | 7/1989 | Oberhardt |
| 4,908,112 A | 3/1990 | Pace |
| 4,909,919 A | 3/1990 | Morris et al. |
| 4,952,518 A | 8/1990 | Johnson et al. |
| 4,963,498 A | 10/1990 | Hillman |
| 4,978,503 A | 12/1990 | Shanks et al. |
| 5,039,617 A | 8/1991 | McDonald et al. |
| 5,073,239 A | 12/1991 | Hjerten |
| 5,077,017 A | 12/1991 | Gorin et al. |
| 5,089,111 A | 2/1992 | Zhu et al. |
| 5,092,973 A | 3/1992 | Zare et al. |
| 5,094,793 A | 3/1992 | Schrenk et al. |
| 5,096,554 A | 3/1992 | Chin |
| 5,096,807 A | 3/1992 | Leaback |
| 5,100,627 A | 3/1992 | Buican et al. |
| 5,108,703 A | 4/1992 | Pfost et al. |
| 5,110,431 A | 5/1992 | Moring |
| 5,112,460 A | 5/1992 | Karger et al. |
| 5,122,248 A | 6/1992 | Karger et al. |
| 5,126,022 A | 6/1992 | Soane et al. |
| 5,132,012 A | 7/1992 | Miura et al. |
| 5,140,161 A | 8/1992 | Hillman et al. |
| 5,141,621 A | 8/1992 | Zare et al. |
| 5,144,139 A | 9/1992 | Hillman et al. |
| 5,147,606 A | 9/1992 | Charlton et al. |
| 5,154,888 A | 10/1992 | Zander et al. |
| 5,164,598 A | 11/1992 | Hillman et al. |
| 5,165,292 A | 11/1992 | Prohaska |
| 5,171,132 A | 12/1992 | Miyazaki et al. |
| 5,171,534 A | 12/1992 | Smith et al. |
| 5,180,480 A | 1/1993 | Manz |
| 5,188,963 A | 2/1993 | Stapleton |
| 5,192,405 A | 3/1993 | Petersen et al. |
| 5,223,219 A | 6/1993 | Subramanian et al. |
| 5,225,163 A | 7/1993 | Andrews |
| 5,229,297 A | 7/1993 | Schnipelsky et al. |
| 5,242,606 A | 9/1993 | Braynin et al. |
| 5,250,263 A | 10/1993 | Manz |
| 5,253,981 A | 10/1993 | Yang et al. |
| 5,271,724 A | 12/1993 | Van Lintel |
| 5,274,240 A | 12/1993 | Mathies et al. |
| 5,277,556 A | 1/1994 | Van Lintel |
| 5,278,048 A | 1/1994 | Parce et al. |
| 5,288,463 A | 2/1994 | Chemelli |
| 5,290,520 A | 3/1994 | Maystre et al. |
| 5,296,114 A | 3/1994 | Manz |
| 5,296,375 A | 3/1994 | Kricka et al. |
| 5,298,134 A | 3/1994 | Zare et al. |
| 5,304,487 A | 4/1994 | Wilding et al. |
| 5,314,593 A | 5/1994 | Swedberg |
| 5,318,680 A | 6/1994 | Fishman et al. |
| 5,320,139 A | 6/1994 | Paul et al. |
| 5,320,730 A | 6/1994 | Ewing et al. |
| 5,322,258 A | 6/1994 | Bosch et al. |
| 5,325,170 A | 6/1994 | Bornhop |
| 5,328,578 A | 7/1994 | Gordon |
| 5,338,427 A | 8/1994 | Shartle et al. |
| 5,346,999 A | 9/1994 | Cathcart et al. |
| 5,375,979 A | 12/1994 | Trah |
| 5,376,252 A | 12/1994 | Ekström et al. |
| 5,384,261 A | 1/1995 | Winkler et al. |
| 5,395,503 A | 3/1995 | Parce et al. |
| 5,410,030 A | 4/1995 | Yue et al. |
| 5,427,946 A | 6/1995 | Kricka et al. |
| 5,429,734 A | 7/1995 | Gajar et al. |
| 5,441,894 A | 8/1995 | Coleman et al. |
| 5,445,939 A | 8/1995 | Anderson |
| 5,460,709 A | 10/1995 | Sarrine et al. |
| 5,478,751 A | 12/1995 | Oosta et al. |
| 5,482,608 A | 1/1996 | Keely et al. |
| 5,486,335 A | 1/1996 | Wilding et al. |
| 5,496,697 A | 3/1996 | Parce et al. |
| 5,498,392 A | 3/1996 | Wilding et al. |
| 5,500,187 A | 3/1996 | Deoms et al. |
| 5,540,889 A | 7/1996 | Gordon et al. |
| 5,556,790 A | 9/1996 | Pettit |
| 5,560,811 A | 10/1996 | Brigges et al. |
| 5,571,410 A | 11/1996 | Swedberg et al. |
| 5,571,680 A | 11/1996 | Chen |
| 5,573,651 A | 11/1996 | Dasgupta et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,595,712 A | 1/1997 | Harbster et al. |
| 5,603,351 A | 2/1997 | Cherukuri et al. |
| 5,605,262 A | 2/1997 | Bond |
| 5,605,662 A | 2/1997 | Heller et al. |
| 5,627,643 A | 5/1997 | Birnbaum et al. |
| 5,632,876 A | 5/1997 | Zanzucchi et al. |
| 5,635,358 A | 6/1997 | Wilding et al. |
| 5,637,458 A | 6/1997 | Frankel et al. |
| 5,637,469 A | 6/1997 | Wilding et al. |
| 5,645,702 A | 7/1997 | Witt et al. |
| 5,650,075 A | 7/1997 | Haas et al. |
| 5,652,149 A | 7/1997 | Mileaf et al. |
| 5,658,723 A | 8/1997 | Oberhardt |
| 5,699,157 A | 12/1997 | Parce |
| 5,716,825 A | 2/1998 | Hancock et al. |
| 5,716,852 A | 2/1998 | Yager et al. |
| 5,726,026 A | 3/1998 | Wilding et al. |
| 5,726,404 A | 3/1998 | Brody |
| 5,731,212 A | 3/1998 | Gavin et al. |
| 5,750,015 A | 5/1998 | Soane et al. |
| 5,755,942 A | 5/1998 | Zanzucchi et al. |
| 5,770,029 A | 6/1998 | Nelson et al. |
| 5,773,298 A | 6/1998 | Lynggaard et al. |
| 5,779,868 A | 7/1998 | Parce et al. |
| 5,780,754 A | 7/1998 | Karlberg et al. |
| 5,783,397 A | 7/1998 | Hughes et al. |
| 5,788,927 A | 8/1998 | Farrell et al. |
| 5,800,690 A | 9/1998 | Chow et al. |
| 5,824,204 A | 10/1998 | Jerman |
| 5,830,681 A | 11/1998 | Hursting et al. |
| 5,833,926 A | 11/1998 | Wurzel et al. |
| 5,834,314 A | 11/1998 | Gates et al. |
| 5,842,787 A | 12/1998 | Kopf-Sill et al. |

(56) References Cited

U.S. PATENT DOCUMENTS

| | | |
|---|---|---|
| 5,846,396 A | 12/1998 | Zanzucchi et al. |
| 5,849,598 A | 12/1998 | Wilson et al. |
| 5,852,495 A | 12/1998 | Parce |
| 5,858,187 A | 1/1999 | Ramsey et al. |
| 5,858,188 A | 1/1999 | Soane et al. |
| 5,858,195 A | 1/1999 | Ramsey |
| 5,858,804 A | 1/1999 | Zanzucchi et al. |
| 5,863,708 A | 1/1999 | Zanzucchi et al. |
| 5,863,801 A | 1/1999 | Southgate et al. |
| 5,869,004 A | 2/1999 | Parce et al. |
| 5,872,010 A | 2/1999 | Karger et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,900,130 A | 5/1999 | Benvegnu et al. |
| 5,919,070 A | 7/1999 | Khan et al. |
| 5,942,443 A | 8/1999 | Parce et al. |
| 5,945,334 A | 8/1999 | Basemer et al. |
| 5,948,227 A | 9/1999 | Dubrow |
| 5,948,684 A | 9/1999 | Weigl et al. |
| 5,955,028 A | 9/1999 | Chow |
| 5,955,030 A | 9/1999 | Pettit |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,965,001 A | 10/1999 | Chow et al. |
| 5,969,736 A | 10/1999 | Field et al. |
| 5,972,710 A | 10/1999 | Weigl et al. |
| 5,979,868 A | 11/1999 | Wu et al. |
| 5,980,704 A | 11/1999 | Cherukuri et al. |
| 5,985,119 A | 11/1999 | Zanzucchi et al. |
| 5,998,217 A | 12/1999 | Rao et al. |
| 6,001,229 A | 12/1999 | Ramsey |
| 6,010,607 A | 1/2000 | Ramsey |
| 6,010,608 A | 1/2000 | Ramsey |
| 6,012,902 A | 1/2000 | Parce |
| 6,033,546 A | 3/2000 | Ramsey |
| 6,054,277 A | 4/2000 | Furcht et al. |
| 6,062,261 A | 5/2000 | Jacobson et al. |
| 6,082,891 A | 7/2000 | Schubert et al. |
| 6,086,740 A | 7/2000 | Kennedy |
| 6,107,044 A | 8/2000 | Nikiforov |
| 6,110,343 A | 8/2000 | Ramsey et al. |
| 6,117,634 A | 9/2000 | Langmore et al. |
| 6,126,804 A | 10/2000 | Andresen |
| 6,132,580 A | 10/2000 | Mathies et al. |
| 6,132,685 A | 10/2000 | Kercso et al. |
| 6,134,950 A | 10/2000 | Forster et al. |
| 6,143,152 A | 11/2000 | Simpson et al. |
| 6,149,787 A | 11/2000 | Chow et al. |
| 6,149,815 A | 11/2000 | Sauter |
| 6,153,073 A | 11/2000 | Dubrow et al. |
| 6,156,181 A | 12/2000 | Parce et al. |
| 6,168,948 B1 | 1/2001 | Anderson et al. |
| 6,174,675 B1 | 1/2001 | Chow et al. |
| 6,176,991 B1 | 1/2001 | Nordman |
| 6,186,660 B1 | 2/2001 | Kopf-Sill et al. |
| 6,190,034 B1 | 2/2001 | Nielsen et al. |
| 6,197,595 B1 | 3/2001 | Anderson et al. |
| 6,210,882 B1 | 4/2001 | Landers et al. |
| 6,210,973 B1 | 4/2001 | Pettit |
| 6,213,151 B1 | 4/2001 | Jacobson et al. |
| 6,231,737 B1 | 5/2001 | Ramsey et al. |
| 6,235,175 B1 | 5/2001 | Dubrow et al. |
| 6,235,471 B1 | 5/2001 | Knapp et al. |
| 6,238,538 B1 | 5/2001 | Parce et al. |
| 6,261,431 B1 | 7/2001 | Mathies et al. |
| 6,267,858 B1 | 7/2001 | Parce et al. |
| 6,284,525 B1 | 9/2001 | Mathies et al. |
| 6,287,850 B1 | 9/2001 | Besemer et al. |
| 6,303,343 B1 | 10/2001 | Kopf-Sill |
| 6,306,590 B1 | 10/2001 | Mehta et al. |
| 6,306,659 B1 | 10/2001 | Parce et al. |
| 6,316,201 B1 | 11/2001 | Nikiforov |
| 6,322,683 B1 | 11/2001 | Wolk et al. |
| 6,326,211 B1 | 12/2001 | Anderson et al. |
| 6,342,142 B1 | 1/2002 | Ramsey |
| 6,352,838 B1 | 3/2002 | Krulevitch et al. |
| 6,358,387 B1 | 3/2002 | Kopf-Sill et al. |
| 6,366,924 B1 | 4/2002 | Parce |
| 6,368,871 B1 | 4/2002 | Christel et al. |
| 6,372,484 B1 | 4/2002 | Ronchi et al. |
| 6,379,929 B1 | 4/2002 | Burns et al. |
| 6,395,232 B1 | 5/2002 | McBride |
| 6,399,025 B1 | 6/2002 | Chow |
| 6,399,365 B2 | 6/2002 | Besemer et al. |
| 6,403,338 B1 | 6/2002 | Knapp et al. |
| 6,408,878 B2 | 6/2002 | Unger et al. |
| 6,409,900 B1 | 6/2002 | Parce et al. |
| 6,413,401 B1 | 7/2002 | Chow et al. |
| 6,413,766 B2 | 7/2002 | Landers et al. |
| 6,420,143 B1 | 7/2002 | Kopf-Sill |
| 6,455,682 B1 | 9/2002 | Barron |
| 6,458,259 B1 | 10/2002 | Parce et al. |
| 6,475,363 B1 | 11/2002 | Ramsey |
| 6,479,299 B1 | 11/2002 | Parce et al. |
| 6,488,895 B1 | 12/2002 | Kennedy |
| 6,495,028 B1 | 12/2002 | Xu et al. |
| 6,506,609 B1 | 1/2003 | Wada et al. |
| 6,517,234 B1 | 2/2003 | Kopf-Sill et al. |
| 6,524,830 B2 | 2/2003 | Kopf-Sill |
| 6,534,009 B1 | 3/2003 | Yao |
| 6,534,013 B1 | 3/2003 | Kennedy |
| 6,544,734 B1 | 4/2003 | Briscoe et al. |
| 6,569,382 B1 | 5/2003 | Edman et al. |
| 6,576,459 B2 | 6/2003 | Miles et al. |
| 6,592,821 B1 | 7/2003 | Wada et al. |
| 6,602,472 B1 | 8/2003 | Zimmermann et al. |
| 6,632,619 B1 | 10/2003 | Harrison et al. |
| 6,642,000 B1 | 11/2003 | Strizhkov et al. |
| 6,649,358 B1 | 11/2003 | Parce et al. |
| 6,670,153 B2 | 12/2003 | Stern |
| 6,681,788 B2 | 1/2004 | Parce et al. |
| 6,685,810 B2 | 2/2004 | Noca et al. |
| 6,706,473 B1 | 3/2004 | Edman et al. |
| 6,707,548 B2 | 3/2004 | Kreimer et al. |
| 6,744,038 B2 | 6/2004 | Wang et al. |
| 6,749,734 B1 | 6/2004 | Simpson et al. |
| 6,767,706 B2 | 7/2004 | Quake et al. |
| 6,778,724 B2 | 8/2004 | Wang et al. |
| 6,779,559 B2 | 8/2004 | Parce et al. |
| 6,783,647 B2 | 8/2004 | Culbertson et al. |
| 6,784,420 B2 | 8/2004 | Wang et al. |
| 6,811,668 B1 | 11/2004 | Berndt et al. |
| 6,811,977 B2 | 11/2004 | Wold et al. |
| 6,814,859 B2 | 11/2004 | Koehler et al. |
| 6,815,664 B2 | 11/2004 | Wang et al. |
| 6,815,671 B2 | 11/2004 | Johnston et al. |
| 6,821,771 B2 | 11/2004 | Festoc |
| 6,830,936 B2 | 12/2004 | Anderson et al. |
| 6,833,068 B2 | 12/2004 | Paul et al. |
| 6,833,542 B2 | 12/2004 | Wang et al. |
| 6,848,462 B2 | 2/2005 | Covington et al. |
| 6,849,411 B2 | 2/2005 | Knapp et al. |
| 6,866,759 B2 | 3/2005 | Miles et al. |
| 6,875,403 B2 | 4/2005 | Liu et al. |
| 6,878,255 B1 | 4/2005 | Wang et al. |
| 6,884,395 B2 | 4/2005 | Tooke et al. |
| 6,900,021 B1 | 5/2005 | Harrison et al. |
| 6,913,697 B2 | 7/2005 | Lopez et al. |
| 6,915,679 B2 | 7/2005 | Chien et al. |
| 6,939,451 B2 | 9/2005 | Zhao et al. |
| 6,951,632 B2 | 10/2005 | Unger et al. |
| 6,953,676 B1 | 10/2005 | Wilding et al. |
| 6,958,119 B2 | 10/2005 | Yin et al. |
| 6,960,437 B2 | 11/2005 | Enzelberger et al. |
| 6,994,826 B1 | 2/2006 | Hasselbrink, Jr. et al. |
| 7,007,710 B2 | 3/2006 | Heller et al. |
| 7,010,391 B2 | 3/2006 | Handique et al. |
| 7,026,414 B1 | 4/2006 | Barron et al. |
| 7,037,417 B2 | 5/2006 | Rossier et al. |
| 7,041,481 B2 | 5/2006 | Anderson et al. |

(56) References Cited

U.S. PATENT DOCUMENTS

| | | | |
|---|---|---|---|
| 7,041,509 B2 | 5/2006 | Parce et al. |
| 7,049,579 B2 | 5/2006 | Ozkan et al. |
| 7,060,224 B2 | 6/2006 | Edman et al. |
| 7,068,874 B2 | 6/2006 | Wang et al. |
| 7,070,681 B2 | 7/2006 | Santiago et al. |
| 7,081,622 B2 | 7/2006 | Kameoka et al. |
| 7,105,300 B2 | 9/2006 | Parce et al. |
| 7,105,810 B2 | 9/2006 | Kameoka et al. |
| 7,105,812 B2 | 9/2006 | Zhao et al. |
| 7,111,466 B2 | 9/2006 | Yamashita et al. |
| 7,138,062 B2 | 11/2006 | Yin et al. |
| 7,142,738 B2 | 11/2006 | Lee |
| 7,153,421 B2 | 12/2006 | Koehler et al. |
| 7,153,673 B2 | 12/2006 | Stern |
| 7,155,344 B1 | 12/2006 | Parce et al. |
| 7,156,969 B2 | 1/2007 | Mehta et al. |
| 7,160,423 B2 | 1/2007 | Chien et al. |
| 7,169,601 B1 | 1/2007 | Northrup et al. |
| 7,171,983 B2 | 2/2007 | Chien et al. |
| 7,179,423 B2 | 2/2007 | Böhm et al. |
| 7,198,701 B2 | 4/2007 | Ueda et al. |
| 7,211,184 B2 | 5/2007 | Webster et al. |
| 7,211,442 B2 | 5/2007 | Gilbert et al. |
| 7,214,299 B2 | 5/2007 | Armstrong |
| 7,217,542 B2 | 5/2007 | Tyvoll et al. |
| 7,231,819 B2 | 6/2007 | Jones et al. |
| 7,238,323 B2 | 7/2007 | Knapp et al. |
| 7,238,477 B2 | 7/2007 | Su et al. |
| 7,259,965 B2 | 8/2007 | Chang et al. |
| 7,297,324 B2 | 11/2007 | TeGrotenhuis et al. |
| 7,332,126 B2 | 2/2008 | Tooke et al. |
| 7,343,248 B2 | 3/2008 | Parce et al. |
| 7,344,681 B1 | 3/2008 | Fiechtner et al. |
| 7,371,533 B2 | 5/2008 | Slater et al. |
| 7,381,317 B2 | 6/2008 | Liu et al. |
| 7,391,020 B2 | 6/2008 | Bousse et al. |
| 7,399,396 B2 | 7/2008 | Barron et al. |
| 7,419,575 B2 | 9/2008 | Culbertson et al. |
| 7,425,700 B2 | 9/2008 | Stults et al. |
| 7,449,096 B2 | 11/2008 | Berndt et al. |
| 7,452,713 B2 | 11/2008 | Barlocchi et al. |
| 7,485,454 B1 | 2/2009 | Jury et al. |
| 7,521,186 B2 | 4/2009 | Burd Mehta |
| 7,531,073 B2 | 5/2009 | Barron et al. |
| 7,534,623 B2 | 5/2009 | Landers et al. |
| 7,537,807 B2 | 5/2009 | Craighead et al. |
| 7,544,019 B2 | 6/2009 | Vikner et al. |
| 7,547,510 B2 | 6/2009 | Daniel et al. |
| 7,591,883 B2 | 9/2009 | Kameoka et al. |
| 7,635,454 B2 | 12/2009 | Mastromatteo et al. |
| 7,641,860 B2 | 1/2010 | Matteo |
| 7,659,056 B1 | 2/2010 | De Vos |
| 7,744,762 B2 | 6/2010 | Lazar |
| 7,745,207 B2 | 6/2010 | Jovanovich et al. |
| 7,745,221 B2 | 6/2010 | Butler et al. |
| 7,749,365 B2 | 7/2010 | Nguyen et al. |
| 7,749,737 B2 | 7/2010 | McBride et al. |
| 7,752,895 B2 | 7/2010 | Lesieur |
| 7,784,330 B2 | 8/2010 | Angelescu et al. |
| RE41,762 E | 9/2010 | Lopez et al. |
| RE41,780 E | 9/2010 | Anderson et al. |
| 7,790,124 B2 | 9/2010 | Matteo |
| 7,797,988 B2 | 9/2010 | Schultz et al. |
| 7,828,954 B2 | 11/2010 | Swanson |
| 7,829,025 B2 | 11/2010 | Ganesan et al. |
| 7,833,709 B2 | 11/2010 | Joseph et al. |
| 7,846,315 B2 | 12/2010 | Amirkhanian et al. |
| 7,851,185 B2 | 12/2010 | Dale et al. |
| 7,854,902 B2 | 12/2010 | Matteo |
| 7,867,193 B2 | 1/2011 | McKenna et al. |
| 7,867,194 B2 | 1/2011 | Fiering et al. |
| 7,892,819 B2 | 2/2011 | Wilding et al. |
| RE42,249 E | 3/2011 | Lopez et al. |
| 7,906,758 B2 | 3/2011 | Stults et al. |
| 7,915,030 B2 | 3/2011 | Inoue et al. |
| RE42,315 E | 5/2011 | Lopez et al. |
| 7,987,022 B2 | 7/2011 | Handique et al. |
| 7,998,418 B1 | 8/2011 | Matteo |
| 8,006,554 B2 | 8/2011 | Thorne, IV |
| 8,007,267 B2 | 8/2011 | Gao et al. |
| 8,021,614 B2 | 9/2011 | Huang et al. |
| 8,043,581 B2 | 10/2011 | Ganesan |
| 8,048,623 B1 | 11/2011 | Rublee et al. |
| 8,720,036 B2 * | 5/2014 | Selden ............... B01L 3/502707 29/527.1 |
| 9,012,208 B2 * | 4/2015 | Selden ............... B01L 3/502715 435/259 |
| 2001/0046701 A1 | 11/2001 | Schulte et al. |
| 2002/0012971 A1 | 1/2002 | Mehta |
| 2002/0060156 A1 | 5/2002 | Mathies et al. |
| 2002/0068357 A1 | 6/2002 | Mathies et al. |
| 2002/0123050 A1 | 9/2002 | Poponin |
| 2002/0123133 A1 | 9/2002 | Mehta et al. |
| 2002/0132265 A1 | 9/2002 | Kopf-Sill |
| 2002/0168671 A1 | 11/2002 | Burns et al. |
| 2002/0172969 A1 | 11/2002 | Burns et al. |
| 2003/0000835 A1 | 1/2003 | Witt et al. |
| 2003/0003499 A1 | 1/2003 | Besemer et al. |
| 2003/0008308 A1 | 1/2003 | Enzelberger et al. |
| 2003/0038248 A1 | 2/2003 | Maher et al. |
| 2003/0104430 A1 | 6/2003 | Nerenberg et al. |
| 2003/0224436 A1 | 12/2003 | Nelson et al. |
| 2004/0014117 A1 | 1/2004 | Slepnev |
| 2004/0018530 A1 | 1/2004 | Bowser et al. |
| 2004/0043479 A1 | 3/2004 | Briscoe et al. |
| 2004/0053290 A1 | 3/2004 | Terbrueggen et al. |
| 2004/0081583 A1 | 4/2004 | Berndt et al. |
| 2004/0106130 A1 | 6/2004 | Besemer et al. |
| 2004/0115794 A1 | 6/2004 | Brubaker |
| 2004/0131504 A1 | 7/2004 | Landers et al. |
| 2004/0166525 A1 | 8/2004 | Besemer et al. |
| 2004/0171054 A1 | 9/2004 | Besemer et al. |
| 2004/0224325 A1 | 11/2004 | Knapp et al. |
| 2004/0245445 A1 | 12/2004 | Suzuki |
| 2004/0259100 A1 | 12/2004 | Gunderson et al. |
| 2004/0259106 A1 | 12/2004 | Gunderson et al. |
| 2005/0003421 A1 | 1/2005 | Besemer et al. |
| 2005/0032072 A1 | 2/2005 | Kautzer et al. |
| 2005/0042628 A1 | 2/2005 | Rava et al. |
| 2005/0053944 A1 | 3/2005 | Fuchs et al. |
| 2005/0053952 A1 | 3/2005 | Hong et al. |
| 2005/0084895 A1 | 4/2005 | Besemer et al. |
| 2005/0089953 A1 | 4/2005 | Besemer et al. |
| 2005/0106615 A1 | 5/2005 | Besemer et al. |
| 2005/0106617 A1 | 5/2005 | Besemer et al. |
| 2005/0106618 A1 | 5/2005 | Besemer et al. |
| 2005/0130213 A1 | 6/2005 | Morrison |
| 2005/0170362 A1 | 8/2005 | Wada et al. |
| 2005/0181403 A1 | 8/2005 | Rava et al. |
| 2005/0196779 A1 | 9/2005 | Ho et al. |
| 2005/0202504 A1 | 9/2005 | Anderson et al. |
| 2005/0208646 A1 | 9/2005 | Besemer et al. |
| 2005/0244933 A1 | 11/2005 | Panda et al. |
| 2005/0287572 A1 | 12/2005 | Mathies et al. |
| 2005/0287661 A1 | 12/2005 | Landers |
| 2006/0019274 A1 | 1/2006 | Goel |
| 2006/0040380 A1 | 2/2006 | Besemer et al. |
| 2006/0057029 A1 | 3/2006 | Coassin et al. |
| 2006/0073484 A1 | 4/2006 | Mathies et al. |
| 2006/0147912 A1 | 7/2006 | Corbett et al. |
| 2006/0166223 A1 | 7/2006 | Reed et al. |
| 2006/0166243 A1 | 7/2006 | Su et al. |
| 2006/0177844 A1 | 8/2006 | Ching et al. |
| 2006/0194306 A1 | 8/2006 | Herr et al. |
| 2006/0228717 A1 | 10/2006 | Joyce |
| 2006/0246493 A1 | 11/2006 | Jensen et al. |
| 2006/0246501 A1 | 11/2006 | Northrup |
| 2006/0260941 A1 | 11/2006 | Tan et al. |
| 2007/0026421 A1 | 2/2007 | Sundberg et al. |
| 2007/0042396 A1 | 2/2007 | Park et al. |
| 2007/0099211 A1 | 5/2007 | Aivazachvili et al. |
| 2007/0099288 A1 | 5/2007 | Gao et al. |
| 2007/0111303 A1 | 5/2007 | Inoue et al. |
| 2007/0117092 A1 | 5/2007 | Sadarangani et al. |

(56) References Cited

U.S. PATENT DOCUMENTS

| | | |
|---|---|---|
| 2007/0154895 A1 | 7/2007 | Spaid et al. |
| 2007/0175768 A1 | 8/2007 | Lau et al. |
| 2007/0184456 A1 | 8/2007 | Chee et al. |
| 2007/0196912 A1 | 8/2007 | Facer et al. |
| 2007/0231799 A1 | 10/2007 | Knight et al. |
| 2007/0238112 A1 | 10/2007 | Sohn et al. |
| 2007/0243109 A1 | 10/2007 | Chen et al. |
| 2007/0248958 A1 | 10/2007 | Jovanovich et al. |
| 2007/0292941 A1 | 12/2007 | Handique et al. |
| 2007/0298429 A1 | 12/2007 | Gumbrecht et al. |
| 2008/0003588 A1 | 1/2008 | Hasson et al. |
| 2008/0014576 A1 | 1/2008 | Jovanovich et al. |
| 2008/0038713 A1 | 2/2008 | Gao et al. |
| 2008/0038714 A1 | 2/2008 | Gao et al. |
| 2008/0050804 A1 | 2/2008 | Handique et al. |
| 2008/0108122 A1 | 5/2008 | Paul et al. |
| 2008/0124716 A1 | 5/2008 | Conney et al. |
| 2008/0160525 A1 | 7/2008 | Brown et al. |
| 2008/0160602 A1 | 7/2008 | He et al. |
| 2008/0166727 A1 | 7/2008 | Esfandyarpour et al. |
| 2008/0171325 A1 | 7/2008 | Brown et al. |
| 2008/0171382 A1 | 7/2008 | Brown et al. |
| 2008/0176230 A1 | 7/2008 | Owen et al. |
| 2008/0176289 A1 | 7/2008 | Zeng et al. |
| 2008/0176757 A1 | 7/2008 | Hassibi et al. |
| 2008/0179555 A1 | 7/2008 | Landers et al. |
| 2008/0182301 A1 | 7/2008 | Handique et al. |
| 2008/0193961 A1 | 8/2008 | Easley et al. |
| 2008/0206758 A1 | 8/2008 | Loge |
| 2008/0213770 A1 | 9/2008 | Williams et al. |
| 2008/0219890 A1 | 9/2008 | Lawson et al. |
| 2008/0241841 A1 | 10/2008 | Murakawa et al. |
| 2008/0241844 A1 | 10/2008 | Kellogg |
| 2008/0277387 A1 | 11/2008 | Landers et al. |
| 2008/0277595 A1 | 11/2008 | Lundquist et al. |
| 2008/0280285 A1 | 11/2008 | Chen et al. |
| 2009/0005259 A1 | 1/2009 | Drmanac |
| 2009/0011416 A1 | 1/2009 | Drmanac |
| 2009/0020427 A1 | 1/2009 | Tan et al. |
| 2009/0023603 A1 | 1/2009 | Selden et al. |
| 2009/0035770 A1 | 2/2009 | Mathies et al. |
| 2009/0036316 A1 | 2/2009 | Drmanac |
| 2009/0042241 A1 | 2/2009 | Yu-Chong et al. |
| 2009/0047713 A1 | 2/2009 | Handique |
| 2009/0053726 A1 | 2/2009 | Owen et al. |
| 2009/0059222 A1 | 3/2009 | Tan et al. |
| 2009/0061489 A1 | 3/2009 | Hanagata et al. |
| 2009/0082552 A1 | 3/2009 | Bynum et al. |
| 2009/0087884 A1 | 4/2009 | Beerling et al. |
| 2009/0092989 A1 | 4/2009 | Chang et al. |
| 2009/0111115 A1 | 4/2009 | Drmanac et al. |
| 2009/0130658 A1 | 5/2009 | Barlag et al. |
| 2009/0130719 A1 | 5/2009 | Handique |
| 2009/0148910 A1 | 6/2009 | Korampally et al. |
| 2009/0170092 A1* | 7/2009 | Landers et al. .......... 435/6 |
| 2009/0186344 A1 | 7/2009 | Farinas |
| 2009/0211908 A1 | 8/2009 | Farinas |
| 2009/0220984 A1 | 9/2009 | Dinges |
| 2009/0222212 A1 | 9/2009 | Curran |
| 2009/0229983 A1 | 9/2009 | Tan et al. |
| 2009/0255601 A1 | 10/2009 | Baeuerle et al. |
| 2009/0258415 A1 | 10/2009 | Bryning et al. |
| 2009/0275034 A1 | 11/2009 | Kiani et al. |
| 2009/0286245 A1 | 11/2009 | Bjornson et al. |
| 2009/0291435 A1 | 11/2009 | Unger et al. |
| 2009/0294287 A1 | 12/2009 | Morita et al. |
| 2009/0317806 A1 | 12/2009 | Hasson |
| 2009/0317824 A1 | 12/2009 | Woudenberg et al. |
| 2009/0317874 A1 | 12/2009 | Dale et al. |
| 2010/0021910 A1 | 1/2010 | Cao et al. |
| 2010/0028980 A1 | 2/2010 | Hasson et al. |
| 2010/0029915 A1 | 2/2010 | Duthie et al. |
| 2010/0032582 A1 | 2/2010 | Xia et al. |
| 2010/0055766 A1 | 3/2010 | Hwang et al. |
| 2010/0068765 A1 | 3/2010 | Zeng et al. |
| 2010/0086925 A1 | 4/2010 | Lee et al. |
| 2010/0086991 A1 | 4/2010 | Fish |
| 2010/0105040 A1 | 4/2010 | Lau et al. |
| 2010/0112645 A1 | 5/2010 | Clark et al. |
| 2010/0120129 A1 | 5/2010 | Amshey et al. |
| 2010/0129896 A1 | 5/2010 | Knapp et al. |
| 2010/0152066 A1 | 6/2010 | Malik et al. |
| 2010/0159576 A1 | 6/2010 | Song et al. |
| 2010/0167288 A1 | 7/2010 | Gale et al. |
| 2010/0167299 A1 | 7/2010 | Korlach |
| 2010/0173310 A1 | 7/2010 | Bousse et al. |
| 2010/0184020 A1 | 7/2010 | Beer |
| 2010/0233675 A1 | 9/2010 | Barrault et al. |
| 2010/0240044 A1 | 9/2010 | Kumar et al. |
| 2010/0243916 A1 | 9/2010 | Maurer et al. |
| 2010/0267013 A1 | 10/2010 | Su et al. |
| 2010/0267585 A1 | 10/2010 | Terbrueggen |
| 2010/0285578 A1 | 11/2010 | Selden et al. |
| 2010/0291666 A1 | 11/2010 | Collier et al. |
| 2010/0303687 A1 | 12/2010 | Blaga et al. |
| 2010/0307921 A1 | 12/2010 | Frazier |
| 2010/0311060 A1 | 12/2010 | Facer et al. |
| 2010/0323912 A1 | 12/2010 | Korlach et al. |
| 2010/0331194 A1 | 12/2010 | Turner et al. |
| 2011/0005932 A1 | 1/2011 | Jovanovich et al. |
| 2011/0014605 A1 | 1/2011 | Stone |
| 2011/0020920 A1 | 1/2011 | Mathies et al. |
| 2011/0027873 A1 | 2/2011 | Cho et al. |
| 2011/0033854 A1 | 2/2011 | Drmanac et al. |
| 2011/0039303 A1 | 2/2011 | Jovanovich et al. |
| 2011/0045503 A1 | 2/2011 | Gee et al. |

FOREIGN PATENT DOCUMENTS

| | | | |
|---|---|---|---|
| EP | 0 903 638 A1 | 3/1999 | |
| EP | 1 584 692 A2 | 10/2005 | |
| EP | 1 769 848 A2 | 4/2007 | |
| JP | A-63-234145 | 9/1988 | |
| JP | A-3-21337 | 1/1991 | |
| WO | WO 94/05414 A1 | 3/1994 | |
| WO | WO 96/03206 A1 | 2/1996 | |
| WO | WO 96/04547 A1 | 2/1996 | |
| WO | WO 96/12541 A1 | 5/1996 | |
| WO | WO 96/30113 A1 | 10/1996 | |
| WO | WO97/02357 * | 1/1997 | .......... C12P 19/34 |
| WO | WO 97/02357 A1 | 1/1997 | |
| WO | WO 97/12665 A1 | 4/1997 | |
| WO | WO 97/16239 A1 | 5/1997 | |
| WO | WO 97/28894 A1 | 8/1997 | |
| WO | WO 97/38300 A1 | 10/1997 | |
| WO | WO 98/54568 A1 | 12/1998 | |
| WO | WO 99/09042 A2 | 2/1999 | |
| WO | WO 99/46591 A2 | 9/1999 | |
| WO | WO 99/61894 A1 | 12/1999 | |
| WO | WO 99/64620 A2 | 12/1999 | |
| WO | WO 00/10015 A1 | 2/2000 | |
| WO | WO 00/45172 A1 | 8/2000 | |
| WO | WO 01/06370 A1 | 1/2001 | |
| WO | WO 02/38809 A1 | 5/2002 | |
| WO | WO 03/042410 A1 | 5/2003 | |
| WO | WO 2005/094981 A1 | 10/2005 | |
| WO | WO2007/047336 A2 | 4/2007 | |
| WO | WO 2008/005248 A2 | 1/2008 | |
| WO | WO 2008/143646 A2 | 11/2008 | |
| WO | WO 2010/041088 A1 | 4/2010 | |
| WO | WO 2010/141139 A1 | 12/2010 | |

OTHER PUBLICATIONS

Easley et al. (PNAS, 2006, 103(51):19272-19277).*
Thaitrong et al. (Anal Chem, 2009, 81, 1371-1377).*
Huang et al. (Electrophoresis, 2006, 27, 3297-3305).*
Paegel et al. (Curr Opin Biotech 2003, 14:42-50).*
Legendre et al. (Analytical Chemistry, 2006, 78, p. 1444-1451).*
Waters et al. (Anal Chem, 1998, vol. 70, p. 158-162).*
Sadler et al. (IEEE Transactions on Components and Packaging Technologies, 2003, 26(2):309-316).*

(56) References Cited

OTHER PUBLICATIONS

"AOTF-Based Multicolor Fluorescence Detection for Short Tandem Repeat (STR) Analysis in an Electrophoreti Microdevice", Journal of Royal Society of Chemistry 2008, Lab Chip, Aug. 2008, 1285-1291.
U.S. Appl. No. 12/659,251, filed Mar. 2, 2010.
U.S. Appl. No. 12/659,492, filed Mar. 10, 2010.
Jun. 30, 2010 International Search Report issued in International Application No. PCT/US2010/026791.
Jan. 31, 2012 International Search Report issued in International Application No. PCT/US2011/056357.
Jan. 31, 2012 Written Opinion of the International Searching Authority issued in International Application No. PCT/US2011/056357.
Jun. 30, 2010 International Search Report issued in International Application No. PCT/US2010/025904.
Jun. 30, 2010 Written Opinion of the International Searching Authority issued in International Application No. PCT/US2010/025904.
Jun. 30, 2010 International Search Report issued in International Application No. PCT/US2010/026801.
Jun. 30, 2010 Written Opinion of the International Searching Authority issued in International Application No. PCT/US2010/026801.
Phillips, "Analysis of Single-cell cultures by immunoaffinity capillary electrophoresis with laser-induced fluorescence detection", Luminescence 2001, vol. 16, pp. 145-152.
Malcik et al., "The performance of a microchip-based fiber optic detection technique for the determination of $Ca^{2+}$ ions in urine", Science Direct, 2005, B 107, pp. 24-31.
Bellon et al., "Feasibility and Performances of a New, Multiplexed, Fast and Low-Cost Fiber-Optic NIR Spectrometer for the On-Line Measurement of Sugar in Fruits", Applied Spectroscopy, Jul. 1993, vol. 47, No. 7, pp. 1079-1083.
Daegupta et al., "Electroosmosis: A Reliable Fluid Propulsion System for Flow Injection Analysis", Anal. Chem. 1994, vol. 66, pp. 1792-1798.
Manz et al., "Miniaturized Total Chemical Analysis Systems: a Novel Concept for Chemical Sensing", Sensors and Actuators, 1990, vol. B1, pp. 244-248.
Jacobson et al, "Effects of Injection Schemes and Column Geometry on the Performance of Microchip Electrophoresis Devices", Anal. Chem., Apr. 1, 1994, vol. 66, No. 7, pp. 1107-1113.
Sandoval, "Method for the Accelerated Measurement of Elecroosmosis in Chemically Modified Tubes for Capillary Electrophoresis", Anal. Chem., Sep. 1, 1996, vol. 68, No. 17, pp. 2771-2775.
Chien et al., "Multiport Flow-Control System for Lab-On-A-Chip Microfluidic Devices", Anal. Chem., 2001, pp. 106-111.
Galambos et al., "An Optical Micro-Fluidic Viscometer", Micro-EL ctr. -Mechanlclcal System (MEMS), Nov. 15-20, 1998, DSC-vol. 66, pp. 187-191.
U.S. Appl. No. 13/064,091, filed Mar. 4, 2011.
U.S. Appl. No. 13/064,093, filed Mar. 4, 2011.
Office Action issued Apr. 17, 2014 in Australian Patent Application No. 2010257126.
German Office Action issued Feb. 11, 2014 in Patent Application No. 11 2010 002 246.1.
Patent Examination Report issued Nov. 18, 2014 in Australian Patent Application No. 2010257126.
European Communication pursuant to Article 94(3) EPC issued Nov. 4, 2015 in European Patent Application No. 10 708 680.3-1356.
Office Action dated Mar. 21, 2016 in Canadian Application No. 2,764,704.

* cited by examiner

DNA ANALYZER

INCORPORATION BY REFERENCE

This application is a continuation of U.S. patent application Ser. No. 12/659,488 filed Mar. 10, 2010, which claims the benefit of U.S. Provisional applications No. 61/213,405, "Fast Sample to Answer DNA Analyzer (Analytical Microdevice)" filed on Jun. 4, 2009, No. 61/213,406, "Optical Approach for Microfluidic DNA Electrophoresis Detection" filed on Jun. 4, 2009, and No. 61/213,404, "Multiple Sample, Integrated Microfluidic Chip for DNA Analysis" filed on Jun. 4, 2009, which are incorporated herein by reference in their entirety.

BACKGROUND

DNA is recognized as the "ultimate biometric" for human identification. DNA analysis can provide evidence for solving forensic and medical cases, such as in areas of criminal justice, identifications of human remains, paternity testing, pathogen detection, disease detection, and the like.

SUMMARY

Aspects of the disclosure provide a microfluidic chip to facilitate DNA analysis. The microfluidic chip can be used in a DNA analyzer for an integrated single chip DNA analysis. The microfluidic chip can include a first domain configured for polymerase chain reaction (PCR) amplification of DNA fragments, a dilution domain configured to dilute a PCR mixture received from the first domain, and a second domain that is coupled to the dilution domain so as to receive the amplified DNA fragments. The second domain includes a separation channel that is configured to perform electrophoretic separation of the amplified DNA fragments. Additionally, the microfluidic chip can include other domains, such as a DNA purification domain, a post-PCR clean-up/dilution domain, and the like.

In an example, the first domain can include a reservoir configured to receive a template DNA and reagents, and generate target DNA fragments based on the template DNA and the reagents. The microfluidic chip can include a plurality of inlets to input the template DNA and the reagents into the microfluidic chip.

In addition to the separation channel, the second domain can include an injection channel configured to inject amplified DNA fragments into the separation channel by electro-kinetic or pressure injection.

The microfluidic chip can also include a plurality of electrode reservoirs for applying electric fields in the separation channel for the electrophoretic separation of the amplified DNA fragments, and for applying electric fields in the injection channel for the electro-kinetic injection. Additionally, the microfluidic chip can include a waste outlet to collect waste liquid generated on the microfluidic chip.

Further, the dilution domain is configured to dilute the PCR mixture received from the first domain according to a ratio from 1:5 to 1:20 (one part of the PCR mixture to 5-20 parts of a dilutant).

Aspects of the disclosure can also provide a cartridge. The cartridge can include a sample acceptor configured to extract a template DNA, and the microfluidic chip. The cartridge can be installed in a DNA analyzer at a time of DNA analysis, and can be thrown away after the DNA analysis. In addition, the cartridge can include a reagent carrier configured to carry reagents required for the PCR amplification, and the electrophoretic separation.

According to the disclosure, the sample acceptor can extract the template DNA by any suitable solid phase extraction or liquid phase extraction, such as silica solid phase extraction, liquid phase enzymatic DNA isolation, and the like. In an example, the sample acceptor includes a well having a liquid phase mixture to extract the template DNA by liquid phase enzymatic DNA isolation. The liquid phase mixture can be sealed in the well before the extraction.

Aspects of the disclosure can provide a DNA analyzer to perform DNA analysis using the microfluidic chip. The DNA analyzer can include an interface for coupling the microfluidic chip to the DNA analyzer, a pressure module configured to flow liquid in the microfluidic chip, a thermal module configured to induce thermal cycles at the first domain of the microfluidic chip for the PCR amplification, a power module configured to generate voltages to be applied to the second domain of the microfluidic chip for the electrophoretic separation, a detection module configured to excite fluorescent labels attached to DNA fragments to emit fluorescence and detect the emitted fluorescence, and a controller module. The controller module can control the pressure module, the thermal module, the power module, and the detection module according to a control procedure to act on the microfluidic chip for a single-chip DNA analysis.

In an embodiment, the pressure module includes a plurality of pumps and/or vacuums configured to inject a template DNA and reagents in the microfluidic chip. The controller module can respectively control the plurality of pumps and/or vacuums. In another embodiment, the microfluidic chip has a membrane valve. The pressure module can include a vacuum pump configured to control the membrane valve to enable fluid movement.

The thermal module includes components to induce thermal cycles for the PCR amplification. In an embodiment, the thermal module includes a heating unit configured to direct heat to the first domain, a cooling unit configured to disperse heat from the first domain, and a sensing unit configured to measure solution temperature in the first domain. In an example, the heating unit includes an infrared light source to direct heat to the first domain, the cooling unit includes a cooling fan, and the sensing unit includes an infrared pyrometer to measure the temperature. Thus, the infrared light source, the cooling fan and the infrared pyrometer can induce the thermal cycles in a reservoir at the first domain for the PCR amplification without contacting the reservoir. In another example, the first domain includes a thermal-coupler reservoir coupled with a PCR reservoir for the PCR amplification. The sensing unit can use any suitable techniques, such as contacting techniques, non-contacting techniques, and the like, to measure solution temperature in the thermal-coupler reservoir. Then, the infrared light source, the cooling fan can induce the thermal cycles in the PCR reservoir for the PCR amplification based on temperature measured from the thermal-coupler reservoir.

In an embodiment, the detection module includes a laser module, a set of optics and a detection module. The laser module is configured to emit a laser beam. The detection module is configured to detect fluorescence. The set of optics is configured to direct the laser beam to the separation channel to excite the fluorescent labels to emit fluorescence, and direct the emitted fluorescence to the detection module for detection.

Additionally, the DNA analyzer can include a mechanism to identify a sample. In an example, the DNA analyzer includes a barcode reader configured to read a barcode to identify a sample. In another example, the DNA analyzer includes a radio frequency identification (RFID) reader configured to read a RFID tag to identify a sample.

Aspects of the disclosure can provide a method for DNA analysis. The method includes inducing thermal cycles in a first domain of a microfluidic chip for PCR amplification of DNA fragments, inducing liquid flow to move the amplified DNA fragments from the first domain to a second domain of the microfluidic chip having a separation channel for electrophoretic separation, inducing an electric field over the separation channel to separate the DNA fragments by size, and detecting the separated DNA fragments.

Additionally, the method can include injecting reagents into a reservoir in the first domain for the PCR amplification, and injecting copies of template DNA into the reservoir for the PCR amplification.

Further, the method can include diluting the amplified DNA fragments in a dilution solution, and electro-kinetically injecting the DNA fragments into the separation channel.

According to an embodiment of the disclosure, the amplified DNA fragments are tagged with fluorescent labels or intercalated with dyes. Thus, to detect the separated DNA fragments, the method can include emitting a laser beam, directing the laser beam to the separation channel to excite the fluorescent labels to emit fluorescence, collecting the emitted fluorescence, and returning the collected fluorescence for detection.

In an embodiment, to assist size measurement, the method can include adding an internal lane standard (ILS) into the amplified DNA fragments.

BRIEF DESCRIPTION OF THE DRAWINGS

Various exemplary embodiments of this disclosure will be described in detail with reference to the following figures, wherein like numerals reference like elements, and wherein.

DETAILED DESCRIPTION OF EMBODIMENTS

Figure 1:
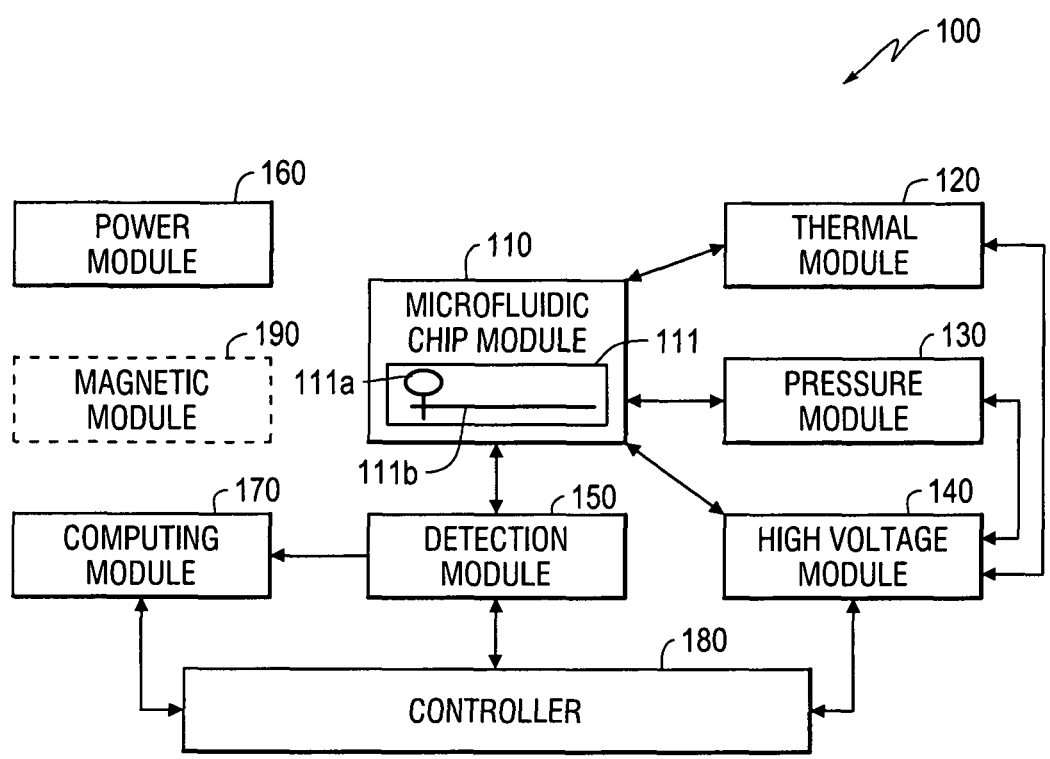
FIG. 1 shows a block diagram of an exemplary DNA analyzer according to an embodiment of the disclosure.

FIG. 1 shows a block diagram of an exemplary DNA analyzer 100 according to an embodiment of the disclosure. The DNA analyzer 100 includes a microfluidic chip module 110, a thermal module 120, a pressure module 130, a high voltage module 140, a detection module 150, a power module 160, a computing module 170, and a controller module 180. Additionally, the DNA analyzer 100 can include a magnetic module 190. These elements can be coupled together as shown in FIG. 1.

The DNA analyzer 100 is capable of processing sample-to-answer DNA analysis on an integrated single-chip. Thus, using the DNA analyzer 100 to perform DNA analysis does not need substantial experience and knowledge of DNA processes. In an example, the appropriate procedures to use the DNA analyzer 100 to perform DNA analysis can be learned in an hour. Additionally, the integrated single-chip DNA analysis requires a reduced volume of reagents, for example, in the order of a micro-liter. Further, the reduced volume of reagents can reduce thermal inputs for inducing thermal cycles in the DNA analysis, and thus reduce the time for DNA analysis.

The microfluidic chip module 110 includes a microfluidic chip 111. The microfluidic chip 111 can be suitably coupled with other elements of the DNA analyzer 100 to perform integrated single-chip DNA analysis. In an example, the microfluidic chip module 110 is implemented as a disposable cartridge, and a cartridge interface that can couple the disposable cartridge with other components of the DNA analyzer 100 that are not included as part of the disposable cartridge. The disposable cartridge includes the microfluidic chip 111 and a micro-to-macro interface. The micro-to-macro interface couples the microfluidic chip 111 to macro structures on the disposable cartridge. The disposable cartridge can be separately stored, and can be installed in the DNA analyzer 100 at a time of DNA analysis. After the DNA analysis, the disposable cartridge can be suitably thrown away.

The microfluidic chip 111 includes various domains that can be suitably configured to enable the integrated single-chip DNA analysis. In an embodiment, DNA analysis generally includes a step of PCR amplification, and a step of electrophoretic separation. The microfluidic chip 111 can include a first domain 111a for the PCR amplification and a second domain 111b for the electrophoretic separation. In addition, the microfluidic chip 111 can include other domains that are suitably integrated with the first domain 111a and the second domain 111b. In an example, the microfluidic chip 111 includes a purification domain fluidically coupled with the first domain 111a. The purification domain can be used to extract and purify a template DNA. It is noted that any suitable techniques, such as solid-phase extraction, liquid-phase extraction, and the like, can be used to purify the template DNA in the purification domain.

In another example, the microfluidic chip 111 includes a post-PCR clean-up/dilution domain that is fluidically coupled with the first domain 111a and the second domain 111b. The post-PCR clean-up/dilution domain can be used for any suitable process after the PCR amplification and before the electrophoretic separation.

The first domain 111a includes a reservoir configured for PCR amplification. In an embodiment, the first domain 111a includes multiple separated reservoirs to enable simultaneous PCR amplification for multiple DNA samples. The temperature at the first domain 111a can be controlled by the thermal module 120 to enable the PCR amplification. According to an embodiment of the disclosure, the PCR amplification on the microfluidic chip 111 requires only a small volume of reagents, and the PCR amplification can achieve rapid thermal cycling. In an example, the volume of reagents used for the PCR amplification can be in the order of sub-micro-liter, and the time required for the PCR amplification can be under 20 minutes.

The second domain 111b can include a plurality of micro channels. The plurality of micro channels can be configured for electrophoretic separation. More specifically, each micro channel can be filled with, for example, polymer sieving matrix. Further, an electric field can be induced in the micro channel. Thus, when DNA fragments are injected in the micro channel, the DNA fragments can migrate by force of the electric field at different speeds based on the sizes of the DNA fragments.

Additionally, the second domain 111b can be configured to facilitate DNA fragments detection in the DNA analysis. In an example, DNA fragments are tagged with fluorescent labels during PCR, before being injected in the micro channels. The fluorescent labels can emit fluorescence of pre-known wavelength when excited by a laser beam. The second domain 111b includes a detection window configured for detection. The laser beam can be directed to pass through the detection window to excite the fluorescent labels in the micro channels. The emitted fluorescence can pass through the detection window to be collected and detected.

The microfluidic chip 111 can include additional structures to facilitate the integrated single-chip DNA analysis. For example, the microfluidic chip 111 can include microfluidic channels that can direct DNA fragments from the first domain 111a to the second domain 111b. Through the microfluidic channels, the DNA fragments flow in a solution from the first domain 111a to the second domain 111b. In addition, the microfluidic chip 111 can include inlets for receiving reagents and the template DNA. The microfluidic chip 111 can also include additional reservoirs for additional processing steps, such as dilution, cleanup, and the like.

The microfluidic chip 111 can be constructed from any suitable material. In an example, the microfluidic chip 111 is constructed from glass. In another example, the microfluidic chip 111 is constructed from plastic or polymeric material.

In addition to the microfluidic chip 111, the disposable cartridge can include a sample acceptor and a reagent carrier. In an example, the sample acceptor accepts a swab used for taking DNA sample, such as from saliva, bloodstains, cigarettes, and the like. Further, the sample acceptor extracts a template DNA from the swab. The sample acceptor can use any suitable mechanism, such as solid-phase extraction, liquid-phase extraction, and the like to obtain and/or purify the template DNA from the swab. In an embodiment, the sample acceptor uses a solid-phase DNA extraction method, such as silica beads based DNA extraction.

In another embodiment, the sample acceptor uses a liquid-phase DNA extraction method. The liquid-phase DNA extraction method can simplify the purification and extraction process, and reduce a total cost of the DNA analyzer 100. In an example, the sample acceptor uses an enzymatic DNA-isolation method to extract and purify the template DNA. The enzymatic DNA-isolation method can achieve liquid phase purification without a need of centrifugation. In addition, the sample acceptor can be suitably designed to maintain sample integrity.

More specifically, the sample acceptor can include a plurality of separated wells for taking swabs, for example. Thus, the DNA analysis can simultaneously process multiple DNA samples. Each well includes a liquid phase mixture that is sealed by a membrane at a bottom portion of the well. The liquid phase mixture can conduct enzymatic digestion of all proteins and other cellular interferences, with the exception of DNA. In an embodiment, the liquid phase mixture can include thermostable proteinases from thermophilic *Bacillus* species. For example, a liquid phase mixture including the thermostable proteinases from thermophilic *Bacillus* species is disclosed in U.S. Patent Application Publication No. 2004/0197788, which is incorporated herein by reference in its entirety. Thus, the liquid phase mixture can perform DNA extraction and purification when a swab is immersed in the liquid phase mixture. The liquid phase method can achieve comparable DNA quality to other methodologies in both DNA concentration and purity. In an example, a final DNA concentration by the liquid phase method is in a range of 0.5-2 ng/µL.

Further, using the liquid phase extraction method instead of the silica solid phase method can reduce the overall hydraulic pressure requirement to induce solution flow through the microfluidic chip 111. In an embodiment, the liquid phase extraction can enable a valveless design for the microfluidic chip 111. Thus, the liquid phase extraction can simplify the DNA analyzer 100 and simplify the manufacturing and testing steps in association with the solid-phase extraction.

Before taking DNA sample, a swab can be sealed in a hard case to avoid contamination. The swab can be attached to a seal cap that can seal the hard case. The swab can be identified by various mechanisms. In an example, a barcode label is attached to the hard case to identify the swab. In another example, the seal cap has a radio frequency identification (RFID) tag implanted. The RFID tag can identify the swab attached to the seal cap throughout the process. After the swab is used to take DNA sample, the swab can be placed in one of the plurality of separated wells, and can be sealed in the well, for example, by the seal cap attached to the sampled swab. In an embodiment, the seal cap is a stepped seal cap that can seal the well in a first step, and a second step. When the seal cap seals the well in the first step, the swab does not puncture the membrane. When the seal cap seals the well in the second step, the swab punctures the membrane and is immersed in the liquid phase mixture. The liquid phase mixture can then extract template DNA from the swab.

The reagent carrier can house a plurality of reagents for DNA analysis, such as reagents for polymerase chain reaction (PCR) amplification, solutions for electrophoretic separation, and the like. In an STR typing example, the reagent carrier houses reagents for multiplexed STR amplification. The reagents can perform multiplexed STR amplification and can use multiple fluorescent dyes to label STR alleles. The reagents can be commercially available reagent kits or can be tailored to the micro-scale chip environment to further facilitate the integrated single-chip DNA analysis.

In addition, the reagent carrier houses solutions that are suitable for electrophoretic separation in the micro-scale chip environment. For example, the reagent carrier houses a coating solution, such as poly-N-hydroxyethylacrylamide, and the like. The coating solution can be used to coat micro channel walls prior to the separation to reduce electro osmotic flow and enable single base pair resolution of amplified DNA fragments. In another example, the reagent carrier houses a dilution solution, such as water and/or Formamide, and the like. The dilution solution can be used to reduce the ionic strength of the sample in order to promote better electro-kinetic injection. In another example, the reagent carrier houses an internal lane standard (ILS). The ILS can be used for accurate size measurements. The reagent carrier also houses a polymer solution for electrophoretic separation in the micro-scale chip environment. The polymer solution is used as gels to provide a physical separation of DNA fragments according to chain length. In an embodiment, the polymer solution can include a sieving or non-sieving matrix. For example, polymer solutions including a sieving or non-sieving matrix are disclosed in U.S. Pat. No. 7,531,073, U.S. Pat. No. 7,399,396, U.S. Pat. No. 7,371,533, U.S. Pat. No. 7,026,414, U.S. Pat. No. 6,811,977 and U.S. Pat. No. 6,455,682, which are incorporated herein by reference in their entirety. In an example, a polymer sieving matrix can be used to yield a single-base resolution in a total separation length of 8 cm and in less than 400 seconds.

The thermal module 120 receives control signals from the controller module 180, and induces suitable temperatures for DNA analysis, such as a temperature for DNA extraction, thermal cycles for the PCR amplification, a temperature for electrophoretic separation, and the like. In an example, the thermal module 120 includes a resistance heater to control a temperature in the wells of the sample acceptor for the DNA extraction and purification. In another example, the thermal module 120 includes another resistance heater to control a temperature at the second domain 111b.

In another example, the thermal module 120 includes a heating unit, a cooling unit and a sensing unit to induce the thermal cycles for the PCR amplification at the first domain 111a. The heating unit can direct heat to the first domain 111a, the cooling unit can disperse heat from the first domain 111a, and the sensing unit can measure a temperature at the first domain 111a. The controller module 180 can control the heating unit and the cooling unit based on the temperature measured by the sensing unit.

In an embodiment, the thermal module 120 performs non-contact thermal controls. For example, the thermal module 120 includes an infrared light source as the heating unit, a cooling fan as the cooling unit, and an infrared pyrometer as the temperature sensing unit. The infrared light source, such as a halogen light bulb, can excite, for example, the 1.3 μm vibrational band of liquid. Thus, the infrared light source can heat a small volume of solution within a reservoir in the first domain 111a independent of the reservoir to achieve rapid heating and cooling. The infrared pyrometer measures blackbody radiation from an outside of the reservoir. In an example, the reservoir is designed to have a thinner side for the infrared pyrometer measurements. The infrared pyrometer measurements at the thinner side can more accurately reflect the temperature of solution within the reservoir. Thus, the DNA analyzer 100 can achieve a precise temperature control along with rapid thermal cycles. In an example, the DNA analyzer 100 can achieve a temperature fluctuation of less than ±0.1° C., and a time of the thermal cycles for the PCR amplification can be less than 20 minutes.

The pressure module 130 receives control signals from the controller module 180, and applies suitable pressures to the microfluidic chip module 110 to enable fluid movement. In an embodiment, the pressure module 130 receives a sensing signal that is indicative of a pressure applied to the microfluidic chip module 110, and suitably adjusts its operation to maintain the suitable pressure to the microfluidic chip module 110.

The pressure module 130 can include a plurality of pumps. The plurality of pumps control the injection of the various reagents and the template DNA solutions into the microfluidic chip 111. According to an embodiment of the disclosure, the plurality of pumps can be individually controlled to achieve any possible timing sequence.

The pressure module 130 may include other pressure components to suit the integrated single-chip integrated DNA analysis. In an embodiment, the microfluidic chip 111 has membrane valves. The pressure module 130 can include a hydrodynamic pressure/vacuum system to suitably control the closing and opening of the membrane valves to enable fluid movement through the microfluidic chip 111.

In another embodiment, the microfluidic chip 111 is valveless. For example, the DNA analyzer 100 uses a liquid phase DNA extraction instead of a silica solid phase DNA extraction. The liquid phase DNA extraction can be integrated with following DNA processes on a valveless microfluidic chip. Thus, the hydrodynamic pressure/vacuum system is not needed. The pressure module 130 can be simplified to reduce the footprint, the weight, the cost, and the complexity of the DNA analyzer 100.

The power module 160 receives a main power, and generates various operation powers for various components of the DNA analyzer 100. In an example, the DNA analyzer 100 is implemented using a modular design. Each module of the DNA analyzer 100 needs an operation power supply, which can be different from other modules. The power module 160 receives an AC power input, such as 100-240 V, 50-60 Hz, single phase AC power from a power outlet. Then, the power module 160 generates 5 V, 12 V, 24 V, and the like, to provide operation powers for the various components of the DNA analyzer 100.

In addition, the power module 160 generates high voltages, such as 1000 V, 2000 V, and the like, for suitable DNA processes on the microfluidic chip 111, such as electro-kinetic injection, electrophoretic separation, and the like.

Further, the power module 160 can implement various protection techniques, such as power outrage protection, graceful shut-down, and the like, to protect the various components and data against power failure. It is noted that the power module 160 may include a back-up power, such as a battery module, to support, for example, graceful shut-down.

The high voltage module 140 can receive the high voltages from the power module 160 and suitably apply the high voltages on the microfluidic chip 111. For example, the high voltage module 140 includes interfaces that apply the high voltages to suitable electrodes on the microfluidic chip 111 to induce electro-kinetic injection and/or electrophoretic separation.

The detection module 150 includes components configured to suit the integrated single-chip DNA analysis. In an embodiment, the detection module 150 is configured for multicolor fluorescence detection. The detection module 150 includes a laser source unit, a set of optics and a detector unit.

The laser source unit emits a laser beam. In an example, the laser source unit includes an argon-ion laser unit. In another example, the laser source unit includes a solid state laser, such as a coherent sapphire optically pumped semiconductor laser unit. The solid state laser has the advantages of reduced size, weight and power consumption.

The set of optics can direct the laser beam to pass through the detection window at the second domain 111b of the microfluidic chip 111. The laser beam can excite fluorescent labels attached to DNA fragments to emit fluorescence. Further, the set of optics can collect and direct the emitted fluorescence to the detector unit for detection. In an STR typing example, STR alleles are separated in the second domain 111b according to sizes. STR alleles of different sizes pass the detection window at different times. In addition, STR alleles of overlapping sizes can be tagged with fluorescent labels of different colors. The detector unit can be configured to detect an STR allele having a fluorescent label based on a time of fluorescence emitted by the fluorescent label and a color of the emitted fluorescence.

In another example, internal lane standard (ILS) is added to migrate in the micro channel with the STR alleles. The ILS includes DNA fragments of known sizes, and can be tagged with a pre-determined fluorescent dye. The detector unit detects fluorescence emitted from the ILS to set up a size scale. In addition, the detector unit detects fluorescence emitted from the STR alleles. The detector unit can suitably convert the detected fluorescence into electrical signals. The electrical signals can be suitably stored and/or analyzed. In an example, a processor executes DNA analysis software instructions to identify the STR alleles by their sizes and emitted fluorescence colors (wavelengths).

The computing module 170 includes computing and communication units. In an example, the computing module 170 includes a personal computer. The personal computer can be coupled with the controller module 180 to provide a user interface. The user interface can inform the status of the DNA analyzer 100, and can receive user instructions for controlling the operation of the DNA analyzer 100. The personal computer includes various storage media to store software instruction and data. The personal computer can include DNA analysis software that can perform data processing based on raw data obtained from the detection module 150. In addition, the personal computer can be coupled to external processing units, such as a database, a server, and the like to further process the data obtained from the DNA analyzer 100.

The magnetic module 190 can enable a magnetic solid phase for the integrated single chip DNA analysis. In an embodiment, the magnetic solid phase can be suitably incorporated in the integrated single chip DNA analysis to facilitate a volume reduction to suit for low copy numbers of template DNAs. In another embodiment, the magnetic solid phase can be suitably incorporated into an integrated single chip sequencing DNA analysis.

The controller module 180 can receive status signals and feedback signals from the various components, and provide control signals to the various components according to a control procedure. In addition, the controller module 180 can provide the status signals to, for example, the personal computer, to inform the user. Further, the controller module 180 can receive user instructions from the personal computer, and may provide the control signals to the various components based on the user instructions.

During operation, the controller module 180 receives user instructions from the personal computer to perform a STR typing analysis, for example. The controller module 180 then monitors the microfluidic chip module 110 to check whether a suitable disposable cartridge has been installed, and whether swabs have been identified and suitably immersed in the liquid phase mixture to extract template DNA. When the controller module 180 confirms the proper status at the microfluidic chip module 110, the controller module 180 starts a control procedure corresponding to the STR typing analysis. In an example, the controller module 180 can control the thermal module 120 to maintain an appropriate temperature at the wells of the sample acceptor for a predetermined time. The liquid phase mixture in the wells can extract template DNAs from the swabs. Then, the controller module 180 can control the pressure module 130 to pump the extracted template DNAs into the first domain 111a of the microfluidic chip 111. In addition, the controller module 180 can control the pressure module 130 to pump reagents for multiplexed STR amplification into the first domain 111a.

Further, the controller module 180 can control the thermal module 120 to induce thermal cycling for the multiplexed STR amplification at the first domain 111a. The reagents and the thermal cycling can cause DNA amplification. In addition, the DNA amplicons can be suitably tagged with fluorescent labels.

Subsequently, the controller module 180 can control the pressure module 130 to flow the DNA amplicons to the second domain 111b. The controller module 180 may control the pressure module 130 to pump a dilution solution into the microfluidic chip 111 to mix with the DNA amplicons. In addition, the controller module 180 may control the pressure module 130 to pump an ILS into the microfluidic chip 111 to mix with the DNA amplicons.

Further, the controller module 180 controls the high voltage module 140 to induce electro-kinetic injection to inject DNA fragments into the micro channels. The DNA fragments include the amplified targets, and the ILS. Then, the controller module 180 controls the high voltage module 140 to induce electrophoretic separation in the micro channels. Additionally, the controller module 180 can control the thermal module 120 to maintain a suitable temperature at the second domain 111b during separation, for example, to maintain the temperature for denaturing separation of the DNA fragments.

The controller module 180 then controls the detection module 150 to detect the labeled DNA fragments. The detection module 150 can emit and direct a laser beam to the micro channels to excite the fluorescent labels to emit fluorescence. Further, the detection module 150 can detect the emitted fluorescence and store detection data in a memory. The detection data can include a detection time, and a detected color (wavelength), along with a detected intensity, such as a relative magnitude of the detected fluorescence. The detection data can be transmitted to the personal computer for storage. Additionally, the controller module 180 can provide control statuses to the personal computer to inform the user. For example, the controller module 180 can send an analysis completed status to the personal computer when the control procedure is completed.

The DNA analyzer 100 can be suitably configured for various DNA analyses by suitably adjusting the reagents housed by the reagent carrier and the control procedure executed by the controller module 180.

Figure 2A:
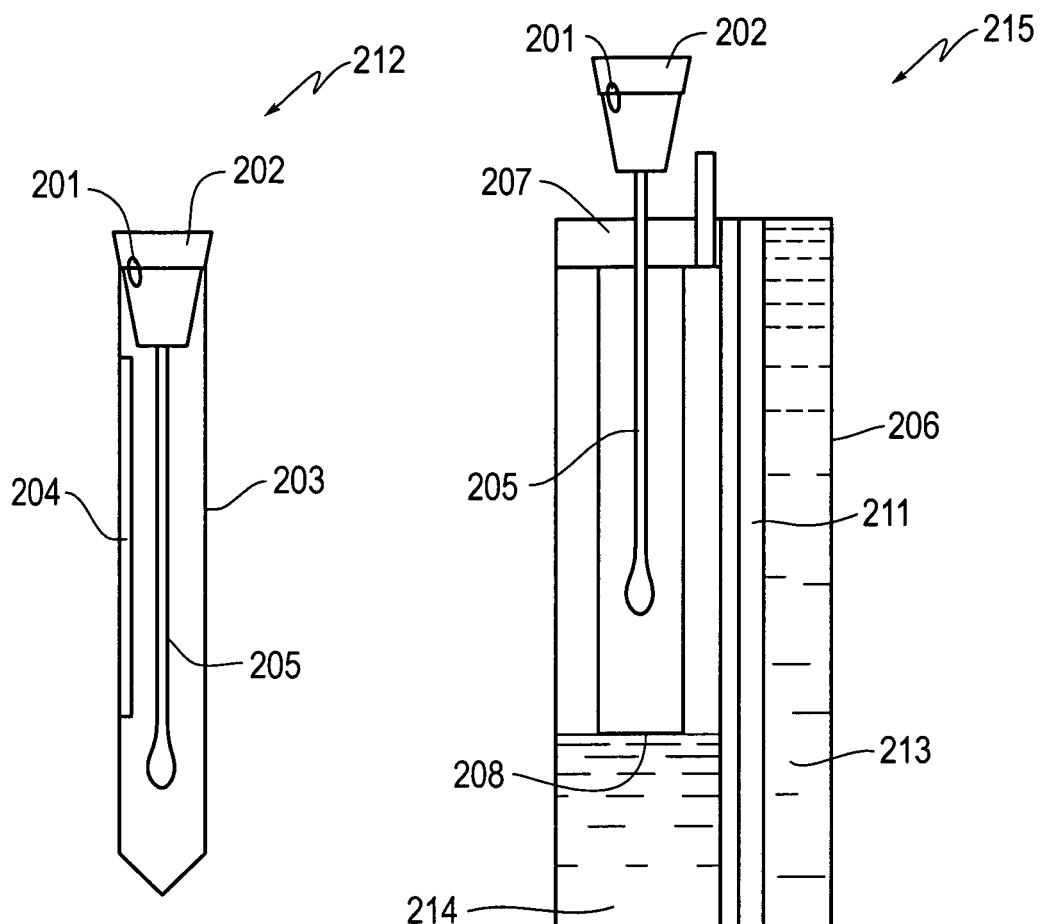
FIGS. 2A-2C show a swab example and elevation views of a sample cartridge example according to an embodiment of the disclosure.
Figure 2B:
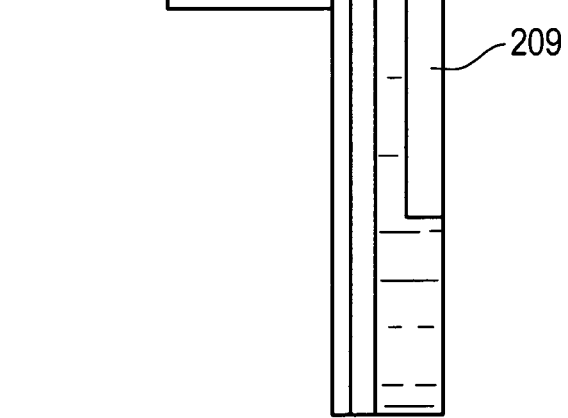
Figure 2C:
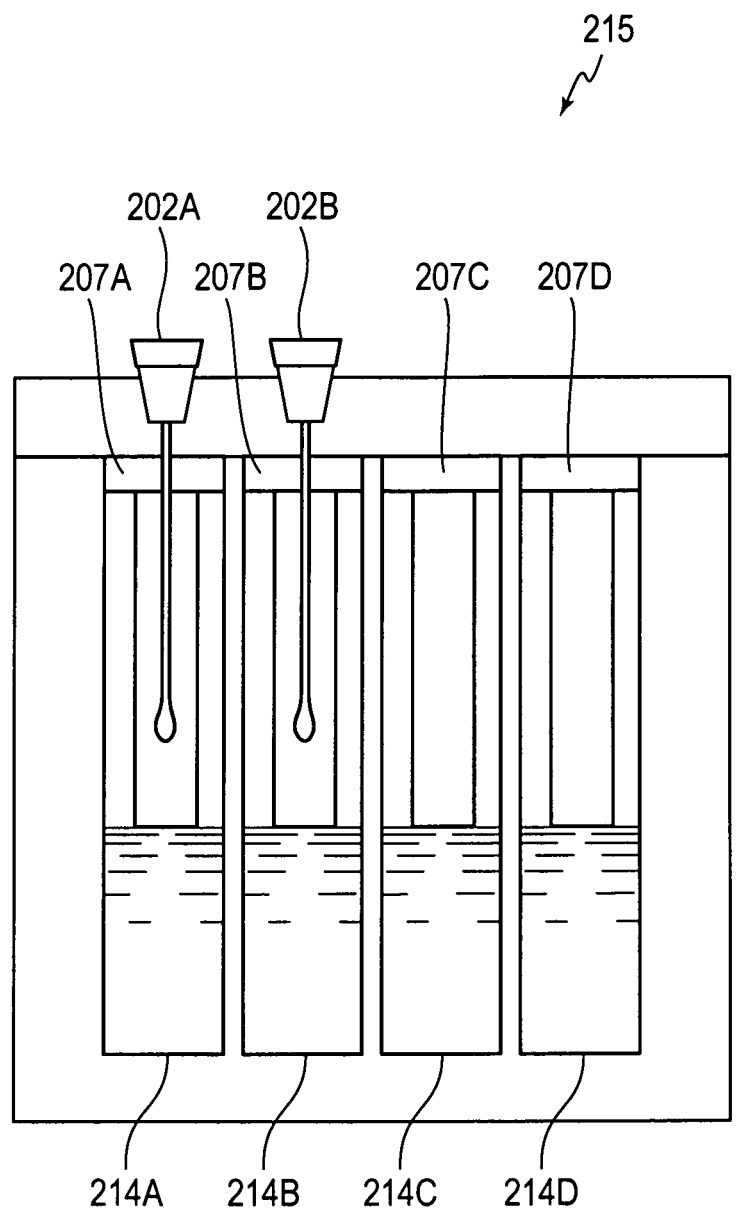

FIG. 2A shows a swab storage example 212, and FIGS. 2B-2C show a side elevation view and a front elevation view of a sample cartridge example 215 according to an embodiment of the disclosure. The swab storage 212 includes a case 203, a seal cap 202 and a swab 205. The seal cap 202 and the swab 205 are attached together. In addition, the swab storage 212 includes an identifier, such as a barcode label 204 that can be attached to the case 203, an RFID tag 201 that can be implanted in the seal cap 202, and the like.

Before taking DNA sample, the swab 205 is safely stored in the case 203 to avoid contamination. After taking DNA sample, the swab 205 can be placed in the sample cartridge 215.

The sample cartridge 215 can include a microfluidic chip 211, a sample acceptor 207 and a reagent carrier 206. The sample acceptor 207 includes a plurality of separated wells 207A-207D for taking swabs. Each well includes a liquid phase mixture 214 that is sealed by a membrane 208 at a bottom portion of the well. The liquid phase mixture 214 can conduct enzymatic digestion of all proteins and other cellular interferences, with the exception of DNA, and thus can perform DNA extraction and purification when a swab with DNA sample is inserted in the liquid phase mixture 214.

While the sample cartridge 215 is described in the context of swabs, it should be understood that the sample cartridge 215 can be suitably adjusted to suit other DNA gathering methods, such as blood stain cards, airborne samples, fingerprints samples, and the like.

In an embodiment, the seal cap 202 is a stepped seal cap that can seal the well in a first step, and a second step. When the seal cap 202 seals the well in the first step, the swab 205 does not puncture the membrane 208, and can be safely sealed in the well to maintain sample integrity. When the seal cap 202 seals the well in the second step, the swab 205 punctures the membrane 208 and is immersed in the liquid phase mixture 214.

The reagent carrier 206 houses various solutions for DNA analysis. In an STR typing example, the reagent carrier houses reagents for multiplexed STR amplification. In addition, the reagent carrier houses a coating solution, such as poly-N-hydroxyethylacrylamide, and the like. The coating solution can be used to coat micro channel walls prior to the separation. Further, the reagent carrier houses a dilution solution, such as water, formamide, and the like. The dilution solution can be used to reduce the ionic strength in order to promote better electro-kinetic injection. In an embodiment, the reagent carrier houses an internal lane standard (ILS). The ILS can be used for size measurement. The reagent carrier also houses a polymer solution for electrophoretic separation in the micro-scale chip environment.

During operation, for example, a new disposable cartridge 215 is taken from a storage package, and installed in a DNA analyzer, such as the DNA analyzer 100. Then, a swab 205 can be used to take a DNA sample. The swab 205 is then identified and inserted into one of the wells 207A-207D and sealed in the first step. Additional swabs 205 can be used to take DNA samples, and then identified and inserted into the un-used wells 207A-207D. Further, the DNA analyzer 100 can include a mechanism that can push the seal caps 202 to seal the wells 207A-207D in the second step, thus the swabs 205 can puncture the membrane 208, and immerse in the liquid phase mixture 214.

Figure 3:
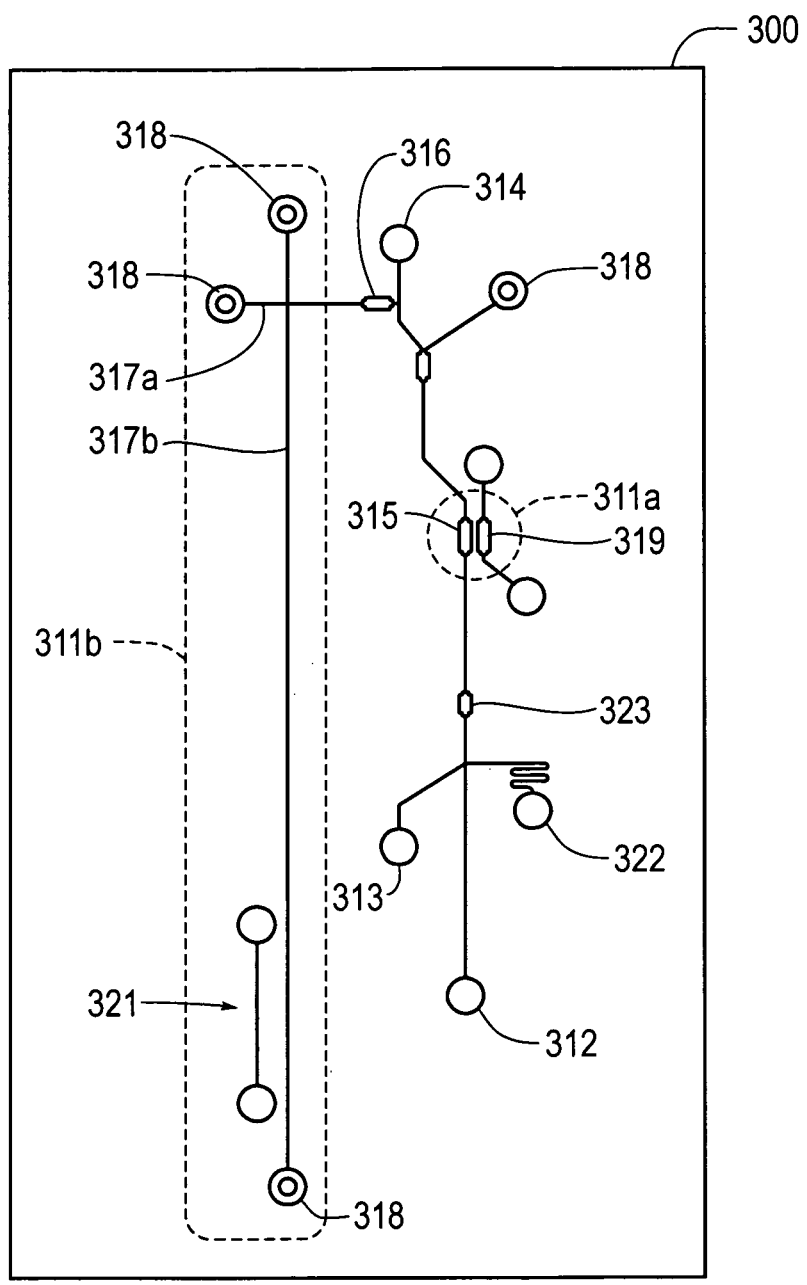
FIG. 3 shows a schematic diagram of a microfluidic chip example according to an embodiment of the disclosure.

FIG. 3 shows a schematic diagram of a microfluidic chip example 311 according to an embodiment of the disclosure. The microfluidic chip 311 includes various micro structures, such as inlets 312-314, reaction reservoirs 315-316, channels 317a-317b, electrode reservoirs 318, outlets (not shown), and the like, that are integrated for single-chip DNA analysis. It is noted that the various micro structures can be designed and integrated to suit for various DNA analyses, such as STR typing, sequencing, and the like.

The inlets 312-314 can be coupled to a pressure module to inject solutions in the microfluidic chip 311. As described above, the connection can be made via a micro-macro interface. In an example, the inlet 312 is for injecting a template DNA solution from a well of the sample acceptor 207, and the inlet 313 is for injecting PCR reagents from the reagent carrier 206. In addition, the inlet 313 can be used for injecting dilution solution and ILS from the reagent carrier 206.

The reaction reservoirs 315-316 are configured for various purposes. In an example, the reaction reservoir 315 is configured for the PCR amplification, and the reaction reservoir 316 is configured for the post-PCR processes, such as dilution, and the like. More specifically, the reaction reservoir 315 is located in a first domain 311a, which is a thermal control domain. The temperature within the thermal control domain 311a can be precisely controlled. In an example, an infrared heating unit directs heat to the thermal control domain 311a, a cooling fan disperses heat from the thermal control domain 311a, and an infrared sensing unit measures a temperature in the thermal control domain 311a. The infrared heating unit and the cooling fan can be controlled based on the temperature measured by the infrared sensing unit. The infrared heating unit, the cooling fan, and the infrared sensing unit can perform thermal control without contacting the thermal control domain 311a.

In another example, the temperature in the thermal control domain 311a is measured by a thermal coupling technique. More specifically, the microfluidic chip 311 includes a thermal-coupler reservoir 319 within the first domain 311a. Thus, the solution temperature within the reaction reservoir 315 and the thermal-coupler reservoir 319 can be closely related. The solution temperature within the thermal-coupler reservoir 319 can be measured by any suitable technique. Based on the measured solution temperature within the thermal-coupler reservoir 319, the solution temperature within the reaction reservoir 315 can be determined. Then, the infrared heating unit and the cooling fan can be controlled based on the temperature measured by the thermal coupling technique in order to control the solution temperature in the reaction reservoir 315.

In an embodiment, after the PCR amplification, the PCR mixture is fluidically directed from the reaction reservoir 315 to a post-PCR clean-up/dilution domain, such as the reaction reservoir 316. In the reaction reservoir 316, the PCR mixture is diluted. In an example, the PCR mixture and a dilutant solution are mixed together according to a ratio from 1:5 to 1:20 (1 part of PCR mixture to 5-20 parts of dilutant). Further, ILS can be added in the reaction reservoir 316 to mix with the PCR mixture.

The channels 317a-317b are located in a second domain 311b. Electric fields can be suitably applied onto the channels 317a-317b. In an example, the channels 317a-317b are configured according to a cross-T design, having a short channel 317a and a long channel 317b.

The electrode reservoirs 318 can be used to apply suitable electric fields over the short channel 317a and the long channel 317b. Thus, the short channel 317a is configured for electro-kinetic injection, and the long channel 317b is configured for electrophoretic separation. For example, when a high voltage is applied to the short channel 317a, DNA fragments can be injected from the reaction reservoir 316 into the short channel 317a at the intersection of the short channel 317a and the long channel 317b. The long channel 317b can be filed with sieving matrix. When a high voltage is applied to the long channel 317b, the injected DNA fragments can migrate in the long channel 317b to the positive side of the electric field induced by the high voltage, in the presence of the sieving matrix. In an example, the length of the long channel 317b is about 8.8 cm with detection at about 8 cm from the intersection.

It should be understood that the microfluidic chip 311 can include other structures to assist DNA analysis. In an example, the microfluidic chip 311 includes an alignment mark 321. The alignment mark 321 can assist a detection module to align to the long channel 317b.

During operation, for example, the inlet 312 can input a template DNA into the reaction reservoir 315, and the inlet 313 can input PCR reagents into the reaction reservoir 315. Then, thermal-cycling can be induced at the first domain 311a, and PCR amplification can be conducted in the reaction reservoir 315 to amplify DNA fragments based on the template DNA and the PCR reagents. After the PCR amplification, the DNA amplicons in the reaction reservoir 315 can be mobilized into the reaction reservoir 316 in a liquid flow. In the reaction reservoir 316, a dilution solution and ILS can be input to mix with the DNA fragments. Further, the DNA fragments in the reaction reservoir 316 can be injected across the short channel 317a by electro-kinetic injection. The DNA fragments then migrate in the long channel 317b under the force of electric field applied over the long channel 317b. The speed of migration depends on the sizes of the DNA amplicons, in the presence of the sieving matrix. Thus, the DNA fragments are separated in the long channel 317b according to their sizes.

Figure 4:
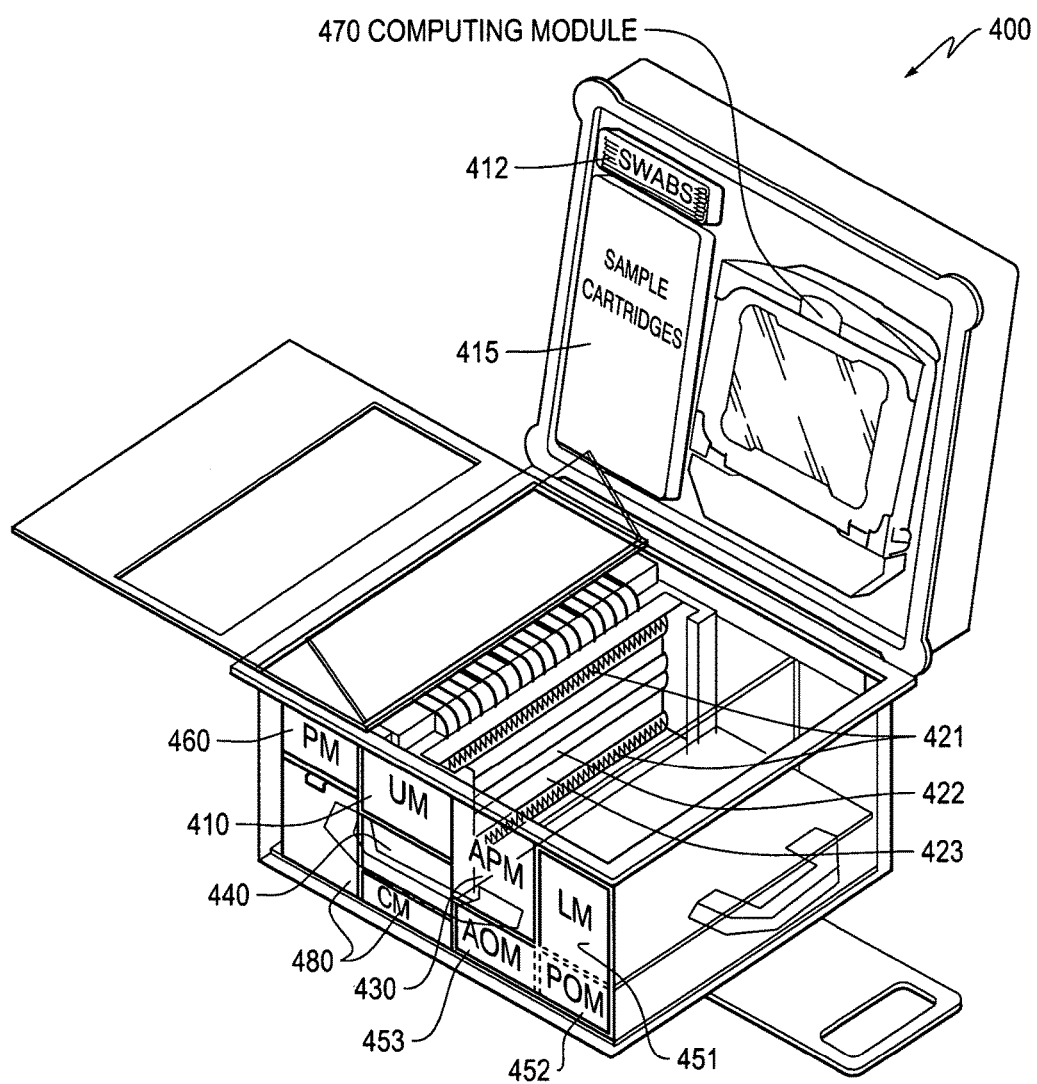
FIG. 4 shows an exemplary DNA analyzer according to an embodiment of the disclosure.

FIG. 4 shows an exemplary DNA analyzer 400 according to an embodiment of the disclosure. The DNA analyzer 400 is packaged in a box. The box includes handles, wheels and the like, to facilitate transportation of the DNA analyzer 400. In an implementation, the total weight of the DNA analyzer 400 is less than 70 lb, and is appropriate for two persons to carry.

The DNA analyzer 400 is implemented in a modular manner. Each module can be individually packaged, and can include an interface for inter-module couplings. Thus, each module can be easily removed and replaced. The modular design can facilitate assembly, troubleshooting, repair, and the like.

The DNA analyzer 400 includes a user module (UM) 410, an active pressure module (APM) 430, a detection module 450, a power module (PM) 460, a computing module 470, and a controller module (CM) 480. In addition, the DNA analyzer 400 includes a sample cartridge storage 415 and a swab storage 412.

The UM 410 includes a holder to hold a sample cartridge, such as the sample cartridge 215, at an appropriate position when the sample cartridge is inserted by a user. Further, the UM 410 includes interface components to couple the sample cartridge 215 with, for example, the APM 430, the detection module 450, and the like. The UM 410 includes thermal components, such as resistance heaters 421, a cooling fan 422, an infrared heating unit 423, and the like. The thermal components can be suitably positioned corresponding to the sample cartridge 215. For example, a resistance heater 421 is situated at a position that can effectively control a temperature of the liquid phase mixture within the plurality of separated wells on the sample cartridge 215. The temperature can be determined to optimize enzyme activities of the liquid phase mixture to conduct enzymatic digestion of all proteins and other cellular interferences, with the exception of DNA. Another resistance heater 421 is at a position that can effectively control a temperature of the separation channel on the microfluidic chip 211. The infrared heating unit is at a position that can direct heat to the thermal control domain of the microfluidic chip 211 on the sample cartridge 215. The cooling fan is at a position that can effectively disperse heat from the thermal control domain. Further, the UM 410 includes a high voltage module that can apply suitable high voltages via the electrode reservoirs of the microfluidic chip 211.

It is noted that the UM 410 can include other suitable components. In an embodiment, the UM 410 includes a magnetic module that can suitably apply magnetic control over a domain of the microfluidic chip 211.

The APM 430 includes suitably components, such as pumps, vacuums, and the like, to apply suitable pressures to the microfluidic chip 211 to enable fluid movement.

The PM 460 receives an input main power, and generates various operation powers, such as 6 V, 12 V, 24 V, 1000V, 2000V, and the like, for various components of the DNA analyzer 400.

The detection module 450 can include a laser module (LM) 451, a passive optics module (POM) 452, and an active optics module (AOM) 453. The LM 451 can include any suitable device to emit a laser beam. In an embodiment, the LM 451 includes an argon-ion laser. In another example, the LM 451 includes a diode laser. In another embodiment, the LM 451 includes a solid state laser, such as a coherent sapphire optically pumped semiconductor laser. The solid state laser can have a reduced size and weight, and can consume less power than the argon-ion laser. In addition, the solid state laser generates less waste heat, such that fan size can be reduced to reduce footprint of the DNA analyzer 400.

The AOM 453 includes optical elements that may need to be adjusted with regard to each inserted microfluidic chip. In an example, the AOM 453 includes a plurality of optical fibers that are respectively coupled to a plurality of separation channels on the microfluidic chip. The plurality of optical fibers can respectively provide laser beams to the plurality of separation channels to excite fluorescence emission. In addition, the plurality of optical fibers can return the emitted fluorescence from the plurality of separation channels.

The POM 452 includes various optical elements, such as lens, splitters, photo-detectors, and the like, that do not need to be adjusted with regard to each inserted microfluidic chip. In an example, the POM 452 is calibrated and adjusted with regard to the LM 451 and the AOM 453 when the detection module 450 is assembled. Then, the optical elements within the POM 452 are situated at relatively fixed positions, and do not need to be adjusted with regard to each inserted microfluidic chip.

The controller module 480 is coupled to the various components of the DNA analyzer 400 to provide control signals for DNA analysis. The controller module 480 includes a control procedure that determines sequences and timings of the control signals.

The computing module 470 is implemented as a personal computer. The personal computer includes a processor, a memory storing suitable software, a keyboard, a display, and a communication interface. The computing module 470 can provide a user interface to ease user control and monitor of the DNA analysis by the DNA analyzer 400.

Figure 5:
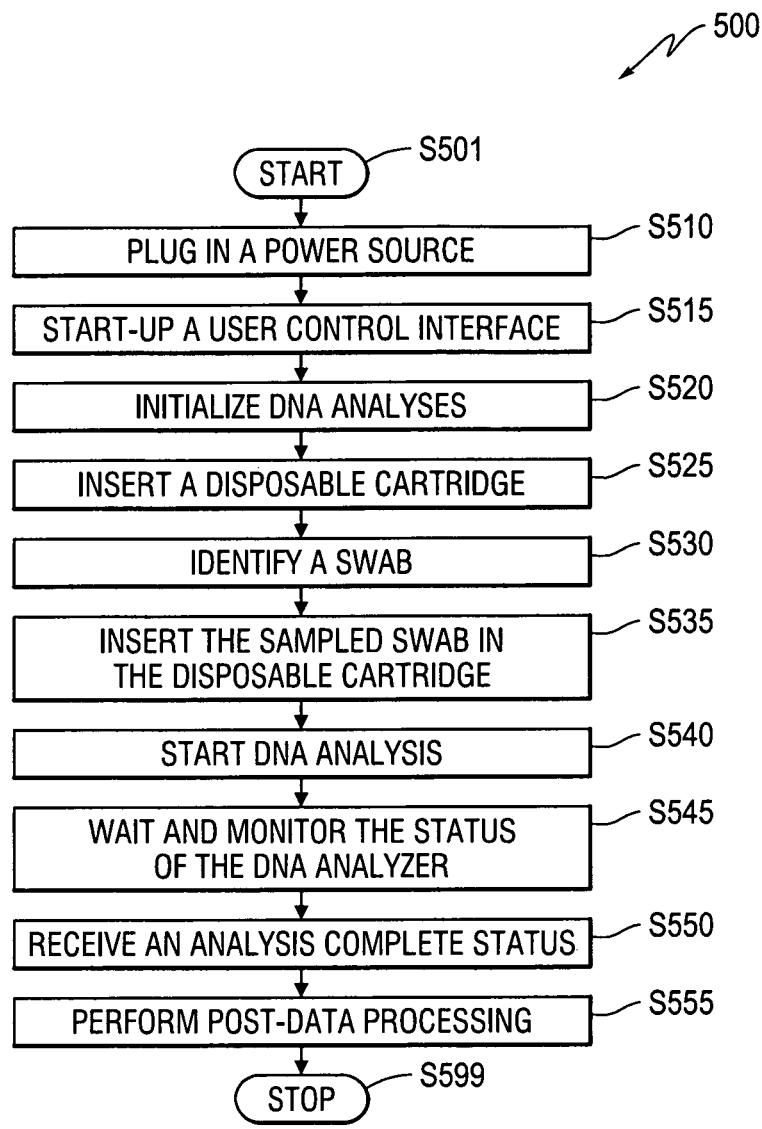
FIG. 5 shows a flow chart outlining an exemplary process for using a DNA analyzer to perform DNA analysis according to an embodiment of the disclosure.

FIG. 5 shows a flow chart outlining a process example for using a DNA analyzer, such as the DNA analyzer 400, to perform DNA analysis according to an embodiment of the disclosure. The process starts at S501, and proceeds to S510.

At S510, a user of the DNA analyzer 400 plugs in a main power supply. In an embodiment, the main power supply can be a 110 V, 50 Hz, AC power supply, or can be a 220V, 60 Hz, AC power supply. The power module 460 can convert the main power supply to a plurality of operation powers, and provide the plurality of operation powers to the various modules of the DNA analyzer 400. Then, the process proceeds to S515.

At S515, the user starts up a user control interface. For example, the user turns on the personal computer 470, and starts a software package that interacts with the user and the controller module 480. The software package enables the personal computer 470 to provide a user control interface on the display. Further, the software package enables the personal computer 470 to receive user instructions via the keyboard or mouse. The software packages can also enable the personal computer 470 to communicate with the controller module 480. Then, the process proceeds to S520.

At S520, the user instructs the DNA analyzer 400 to initialize. The user control interface receives the initialization instruction, and the software package enables the personal computer 470 to send the initialization instruction to the controller module 480. The controller module 480 can then initialize the various components of the DNA analyzer 400. For example, the controller module 480 can power on the various components, check the status and reset the status if needed. Then, the process proceeds to S525.

At S525, the user inserts a sample cartridge 215 in the UM 410. The sample cartridge 215 can be positioned by a holder. The interface components can suitably couple the sample cartridge 215 to other components of the DNA analyzer 400. Then, the process proceeds to S530.

At S530, the user takes a swab 205, and lets the DNA analyzer 400 to identify the swab 205. In an example, the DNA analyzer 400 includes a barcode reader that can read the barcode label 204 attached to the case 203 for storing the swab 205. In another example, the DNA analyzer 400 excites the RFID 201 implanted in the seal cap 202 of the swab 205 to obtain a unique serial number of the swab 205. Then, the process proceeds to S535.

At S535, the user uses the swab 205 to take a DNA sample and inserts the swab 205 into a well of the sample cartridge 215. The user may repeat the steps S530 and S535 to insert multiple swabs 205 into the separated wells of the sample cartridge 215. Then, the process proceeds to S540.

At S540, the user instructs the DNA analyzer 400 to start a DNA analysis. The user control interface receives the start instruction, and the software package enables the personal computer 470 to send the start instruction to the controller module 480. The controller module 480 can start a control procedure corresponding to the DNA analysis. In an example, the controller module 480 starts an STR typing procedure corresponding to a multiplexed STR typing analysis. In another example, the controller module 480 starts a sequencing procedure corresponding to DNA sequencing analysis. Then, the process proceeds to S545.

At S545, the user waits and monitors the status of the DNA analysis. The control procedure can specify sequences and timings of control signals to various components of the DNA analyzer 400 corresponding to the DNA analysis. Then, the controller module 480 automatically sends the control signals according to the sequences and the timings specified in the control procedure. In addition, the controller module 480 receives status and feedback signals from the various components, and sends them to the personal computer 470. The personal computer 470 then provides the analysis status for the user to monitor. Then, the process proceeds to S550.

At S550, the controller module 480 finishes executing the control procedure, and sends an analysis-completed status to the personal computer 470. The personal computer 470 can inform the user of the analysis-completed status via the user control interface. Then, the process proceeds to S555.

At S555, the user performs post data processing. The user can store the raw data of the DNA analysis, or transmit the raw data to a remote receiver. In addition, the user may start a software package for post data processing. Alternatively, the software package for post data processing can be suitably integrated with the control procedure. Thus, after the control procedure is successfully executed, the software package for post data processing is executed automatically to perform post data processing. The process then proceeds to S599 and terminates.

It is noted that to perform another DNA analysis, the user may throw away the sample cartridge and repeat S520-S550. It is also noted that the sequence of the DNA analysis steps can be suitably adjusted. For example, S535 and S530 can be swapped, thus a swab can be first used to take a DNA sample, and then identified by the DNA analyzer 400.

Figure 6:
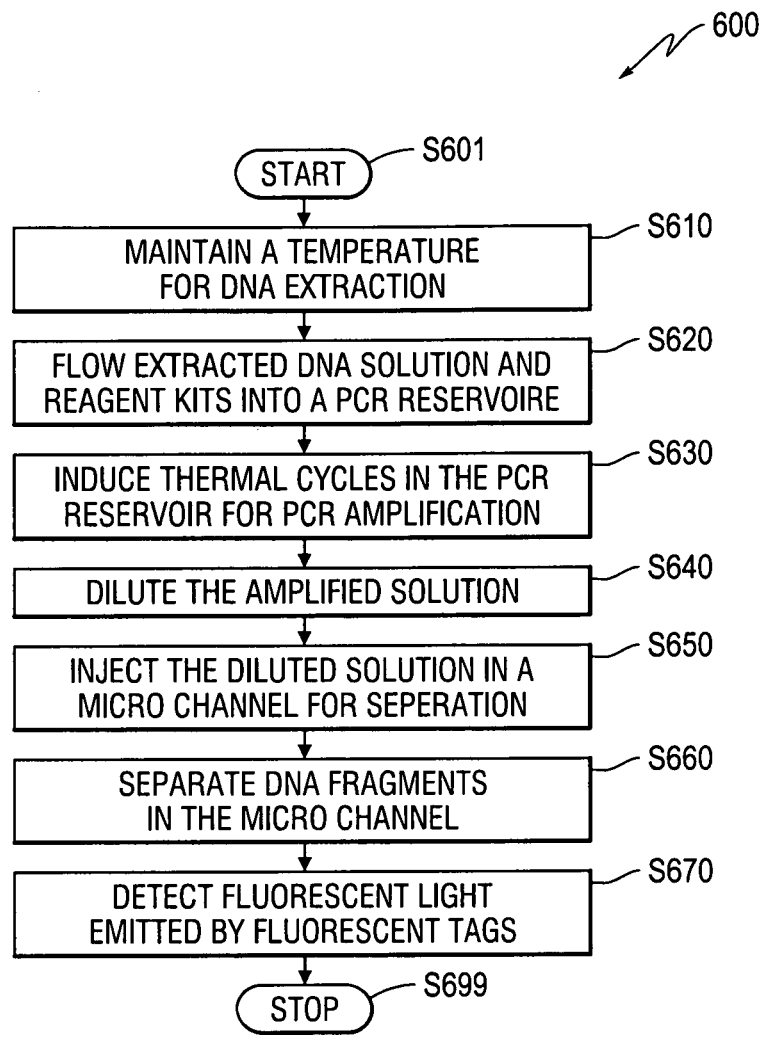
FIG. 6 shows a flow chart outlining an exemplary process for a DNA analyzer to perform DNA analysis according to an embodiment of the disclosure.

FIG. 6 shows a flow chart outlining a process example 600 for a DNA analyzer to perform multiplexed STR typing according to an embodiment of the disclosure. The process starts at S601 and proceeds to S610.

At S610, the controller module 480 controls the resistance heater 421 to maintain a temperature for template DNA extraction and purification. More specifically, the resistance heater 421 is positioned corresponding to the plurality of wells on the sample cartridge 215. A well can accept a swab 205. The swab 205 can puncture the membrane that seals the liquid phase mixture at the bottom of the well, thus the swab 205 is immersed into the liquid phase mixture. The liquid phase mixture can extract and purify a template DNA from the swab at the temperature according to enzymatic DNA isolation method. In an embodiment, the liquid phase mixture can achieve a compatible DNA concentration and purity to silica based solid phase extraction method in about 6 minutes. Then, the process proceeds to S620.

At S620, the controller module 480 controls the APM 430 to flow the extracted template DNA and reagents to a reaction reservoir for the PCR amplification. For example, the reagent carrier 206 houses reagents for multiplexed STR amplification. The controller module 480 sends control signals to the APM 430. In response to the control signals, a pump pumps the liquid phase mixture from the well to the reaction reservoir, and another pump pumps the reagents from the reagent carrier 206 to the reaction reservoir. Then, the process proceeds to S630.

At S630, the controller module 480 controls the cooling fan 422 and the infrared heating unit 423 to induce thermal cycling in the reaction reservoir for the multiplexed STR amplification. In addition, the reagents can attach fluorescent labels to the DNA amplicons during the STR amplification process. The process then proceeds to S640.

At S640, after the PCR amplification, the solution can be diluted. More specifically, the controller module 480 sends control signals to the APM 430 after the PCR amplification. In response to the control signals, the APM 430 flows the DNA amplicons into a dilution reservoir. In addition, the APM 430 flows a dilution solution from the reagent carrier into the dilution reservoir. The process then proceeds to S650.

At S650, the controller module 480 sends control signals to the high voltage module in the UM 410 to inject the DNA amplicons across the injection arm (the short channel 317a). Then, the process proceeds to S660.

At S660, the controller module 480 sends control signals to the high voltage module in the UM 410 to apply appropriate high voltage over the separation channel (the long channel 317b) to separate the DNA amplicons based on sizes. The process then proceeds to S670.

At S670, the controller module 480 sends control signals to the detection module 450 to excite the fluorescent labels to emit fluorescence and detect the emitted fluorescence. The raw detection data can be sent to the personal computer 470 for storage and post-processing. The process then proceeds to S699, and terminates.

It is noted that some process steps in the process 600 can be executed in parallel. For example, the step S660 and the step S670 can be executed in parallel. The controller module 480 sends control signals to both the high voltage module in the UM 410 and the detection module 450 at about the same time. The control signals to the high voltage module in the UM 410 cause the electrophoretic separation in the separation channel, while the control signals to the detection module 450 cause fluorescence detection.

It is noted that the process 600 can be suitably adjusted along with reagents adjustments for other DNA analysis, such as qPCR DNA quantitation, sequencing, and the like.

In a qPCR DNA quantitation example, step S601 to S630 are executed, and step S640 to S670 can be deleted. In addition, in step S630, when thermal cycles are induced in a qPCR reservoir for PCR amplification, the controller module 480 sends control signals to the detection module 450 to detect florescence emitted by the fluorescent labels in the qPCR reservoir.

It is also noted that a magnetic solid phase purification process step can be suitably added into the process 600 to facilitate further volume reduction, thus the process 600 can be adjusted for DNA sequencing.

Figure 7:
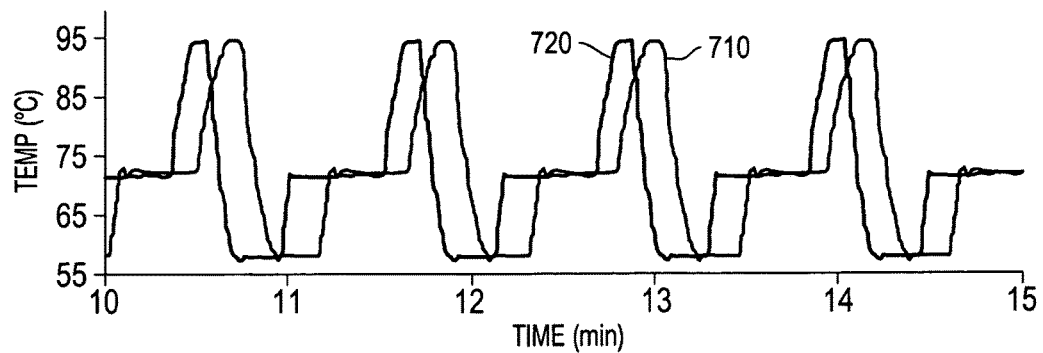
FIG. 7 shows a plot of thermal cycles for polymerase chain reaction (PCR) amplification according to an exemplary DNA analyzer implementation.

FIG. 7 shows a plot of thermal cycling for polymerase chain reaction (PCR) amplification induced in two systems. Thermal cycling 710 is induced in a first system, and thermal cycling 720 is induced in a second system. Each of the thermal cycling 710 and the thermal cycling 720 is induced by an infrared light source and a cooling fan based on a temperature measurement using a thermal-coupler reservoir technique. Both systems achieve a temperature fluctuation of less than $\pm 0.1°$ C. In addition, a system-to-system reproducibility is achieved.

Figure 8:
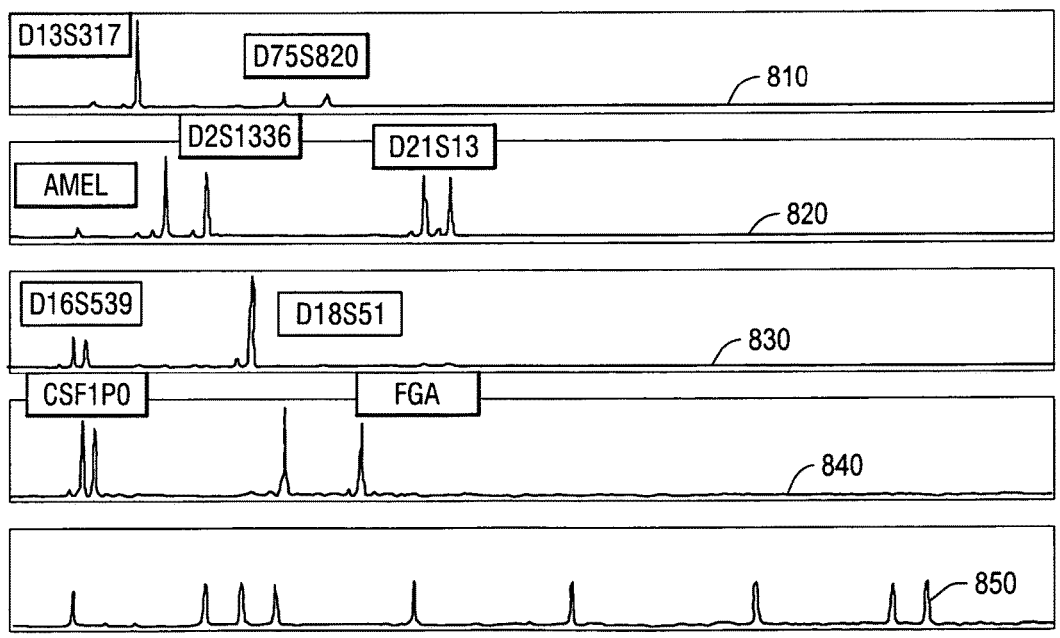
FIG. 8 shows a plot of fluorescent light detection according to an exemplary DNA analyzer implementation.

FIG. 8 shows a plot 800 of a 16-loci STR typing analysis result obtained from an implemented DNA analyzer according to an embodiment of the disclosure. The DNA analyzer accepts a sample, such as in the form of a swab, extracts a template DNA from the sample, and acts on a microfluidic chip to perform an integrated single-chip DNA analysis based on the extracted template DNA. More specifically, the DNA analyzer pumps the extracted template DNA and 16-loci STR reagents in a reservoir within a first domain of the microfluidic chip. Then, the DNA analyzer induces thermal cycling in the first domain of the microfluidic chip to perform multiplexed 16-loci PCR amplification based on the template DNA. The 16-loci STR reagents use four fluorescent labels having different wavelengths to label the DNA fragments. After the PCR amplification, the DNA analyzer pumps ILS into the amplified STR alleles. The ILS is labeled with a fifth fluorescent label having a different wavelength from the four fluorescent labels used by the 16-loci STR reagents. Further, the DNA analyzer injects the STR alleles along with the ILS into a second domain of the microfluidic chip. The second domain includes a separation channel. The DNA analyzer induces an electrical field over the separation channel for electrophoretic separation. Under the electrical field, the STR alleles and the ILS migrate in the separation channel based on sizes. The DNA analyzer then generates and directs a laser beam to the separation channel to excite the fluorescent labels to emit fluorescence. Further, the emitted fluorescence is collected and detected by the DNA analyzer. The DNA analyzer detects fluorescence intensities of different wavelengths over time, and identifies an STR in the sample based on a combination of wavelength and size comparison with ILS.

The plot 800 shows five curves 810-850. The curve 810 shows detected fluorescence intensity versus time for a first wavelength. The curve 820 shows detected fluorescence intensity versus time for a second wavelength. The curve 830 shows detected fluorescence intensity versus time for a third wavelength. The curve 840 shows detected fluorescence intensity versus time for a fourth wavelength, and the curve 850 shows detected fluorescence intensity versus time for a fifth wavelength. The fifth wavelength corresponds to the fluorescent label used to tag the ILS, thus spikes in the curve 850 are of known sizes. Spikes in the curves 810-840 correspond to STR alleles in the sample under analysis. The sizes of the STR alleles can be determined based on comparison to the spikes in the curve 850. Thus, the STR alleles can be identified based on the wavelength and the size comparison with the ILS.

While the invention has been described in conjunction with the specific exemplary embodiments thereof, it is evident that many alternatives, modifications, and variations will be apparent to those skilled in the art. Accordingly, exemplary embodiments of the invention as set forth herein are intended to be illustrative, not limiting. There are changes that may be made without departing from the spirit and scope of the invention.

What is claimed is:

1. A microfluidic chip, comprising:
an inlet configured to receive a template DNA extracted from a sample acceptor that is external of the microfluidic chip and is fluidically coupled to the microfluidic chip on a cartridge;
a first domain configured for polymerase chain reaction (PCR) amplification of DNA fragments, the first domain including a thermal-coupler reservoir coupled with a PCR reservoir for PCR amplification, thermal cycles in the PCR reservoir being induced based on temperature measured from the thermal-coupler reservoir;
a dilution domain having a reservoir that is fluidically coupled to the first domain and is configured to dilute a PCR mixture received from the first domain with a dilutant in the reservoir; and
a second domain that is fluidically coupled to the dilution domain so as to receive the amplified DNA fragments, the second domain including a separation channel that is configured to perform electrophoretic separation of the amplified DNA fragments.

2. The microfluidic chip of claim 1, wherein:
the PCR reservoir is configured to receive a template DNA and reagents, and amplify the DNA fragments based on the template DNA and the reagents.

3. The microfluidic chip of claim 2, further comprising:
a plurality of inlets configured to input the template DNA and the reagents into the microfluidic chip.

4. The microfluidic chip of claim 1, wherein the second domain comprises:
an injection channel configured to inject the amplified DNA fragments into the separation channel by electrokinetic injection.

5. The microfluidic chip of claim 1, further comprising:
a plurality of electrode reservoirs for applying an electric field over the separation channel.

6. The microfluidic chip of claim 1, wherein in the dilution domain, the PCR mixture and the dilutant are mixed according to a ratio from 1:5 to 1:20.

7. A cartridge, comprising:
a sample acceptor external to and fluidically coupled to a microfluidic chip on the cartridge,
the sample acceptor configured to extract a template DNA and the microfluidic chip having a first domain and a second domain coupled to the first domain, wherein the first domain is configured to perform polymerase chain reaction (PCR) amplification of DNA fragments based on the template DNA, and the second domain has a separation channel that is configured to perform electrophoretic separation of the amplified DNA fragments, the first domain includes a thermal-coupler reservoir coupled with a PCR reservoir for PCR amplification, thermal cycles in the PCR reservoir are induced based on temperature measured from the thermal-coupler reservoir.

8. The cartridge of claim 7, further comprising:
a reagent carrier configured to carry reagents for the PCR amplification, and solutions for the electrophoretic separation.

9. The cartridge of claim 7, wherein the sample acceptor is configured to extract the template DNA by at least one of a silica solid phase extraction, and a liquid phase enzymatic DNA isolation.

10. The cartridge of claim 7, wherein the sample acceptor comprises:
a well having a liquid phase mixture to extract the template DNA.

11. The cartridge of claim 10, wherein the liquid phase mixture is sealed in the well before the extraction.

12. The cartridge of claim 8, wherein:
the PCR reservoir is configured to receive the extracted template DNA and the reagents, and amplify the DNA fragments based on the template DNA and the reagents.

13. The cartridge of claim 8, wherein the microfluidic chip further comprises:
a plurality of inlets configured to input the template DNA and the reagents kits into the microfluidic chip.

14. The cartridge of claim 7, wherein the second domain of the microfluidic chip comprises:
an injection channel configured to inject the amplified DNA fragments into the separation channel by electrokinetic injection.

15. The cartridge of claim 7, wherein the microfluidic chip further comprises:
a plurality of electrode reservoirs for applying an electric field over the separation channel.

16. The cartridge of claim 7, wherein the microfluidic chip further comprises:
a waste outlet to drain liquid out of the microfluidic chip.

17. The cartridge of claim 7, wherein the microfluidic chip further comprises:
a dilution domain coupled to the first domain and the second domain, the dilution domain diluting a PCR mixture received from the first domain with a dilutant, and providing the diluted PCR mixture to the second domain.

18. The cartridge of claim 17, wherein in the dilution domain, the PCR mixture and the dilutant are mixed according to a ratio from 1:5 to 1:20.

19. The cartridge of claim 10, wherein the liquid phase mixture is capable of performing enzymatic digestion of proteins and other cellular interferences, with the exception of DNA.

* * * * *